US007319780B2

(12) United States Patent
Fedorovskaya et al.

(10) Patent No.: US 7,319,780 B2
(45) Date of Patent: Jan. 15, 2008

(54) IMAGING METHOD AND SYSTEM FOR HEALTH MONITORING AND PERSONAL SECURITY

(75) Inventors: Elena A. Fedorovskaya, Pittsford, NY (US); Serguei Endrikhovski, Rochester, NY (US); Kenneth A. Parulski, Rochester, NY (US); Carolyn A. Zacks, Rochester, NY (US); Karen M. Taxier, Rochester, NY (US); Michael J. Telek, Pittsford, NY (US); Frank Marino, Rochester, NY (US); Dan Harel, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 671 days.

(21) Appl. No.: 10/304,037

(22) Filed: Nov. 25, 2002

(65) Prior Publication Data
US 2004/0101178 A1 May 27, 2004

(51) Int. Cl.
*G06K 9/00* (2006.01)
(52) U.S. Cl. ...................... 382/128; 128/922
(58) Field of Classification Search ............... 382/100, 382/128, 130–132; 128/922
See application file for complete search history.

(56) References Cited

U.S. PATENT DOCUMENTS

| 5,164,831 | A | 11/1992 | Kuchta et al. |
| 5,477,264 | A | 12/1995 | Sarbadhikari et al. |
| 5,666,215 | A | 9/1997 | Fredlund et al. |
| 5,734,425 | A | 3/1998 | Takizawa et al. |
| 5,742,233 | A | 4/1998 | Hoffman et al. |
| 5,760,917 | A | 6/1998 | Sheridan |
| 5,911,687 | A | * | 6/1999 | Sato et al. .................. 600/300 |
| 6,003,991 | A | 12/1999 | Viirre |
| 6,004,061 | A | 12/1999 | Manico et al. |
| 6,205,716 | B1 | * | 3/2001 | Peltz ......................... 52/36.2 |
| 6,282,231 | B1 | 8/2001 | Norman et al. |
| 6,282,317 | B1 | 8/2001 | Luo et al. |
| 6,287,252 | B1 | 9/2001 | Lugo |
| 6,294,993 | B1 | 9/2001 | Calaman |

(Continued)

FOREIGN PATENT DOCUMENTS

EP 0 467 094 A2 1/1992

(Continued)

OTHER PUBLICATIONS

Angela Chang et al., "LumiTouch: An Emotional Communication Device", lumitouch@media.mit.edu.

(Continued)

*Primary Examiner*—Samir Ahmed
*Assistant Examiner*—Anand Bhatnagar

(57) ABSTRACT

An image capture method is provided. In accordance with the method, an image of the scene is captured and affective information is collected a capture. The scene image and affective information are transmitted to an image receiver. An imaging system is also provided having an image capture system adapted to capture an image of a scene and a memory which stores the captured image. A set of sensors is adapted to collect affective signals from the user at capture. A processor is adapted to determine affective information based upon the affective signals and to associate affective information with the captured image. A transmitter sends the scene image and the affective information to a receiver.

33 Claims, 15 Drawing Sheets

U.S. PATENT DOCUMENTS

| | | | |
|---|---|---|---|
| 6,438,323 | B1 | 8/2002 | DeCecca et al. |
| 6,608,615 | B1 | 8/2003 | Martins |
| 6,996,256 | B2 * | 2/2006 | Pavlidis ............... 382/118 |
| 2001/0056228 | A1 * | 12/2001 | Utsugi et al. ............ 600/300 |
| 2002/0019584 | A1 | 2/2002 | Schulze et al. |
| 2002/0052551 | A1 * | 5/2002 | Sinclair et al. ........... 600/476 |
| 2002/0076100 | A1 | 6/2002 | Luo |
| 2002/0101619 | A1 | 8/2002 | Tsubaki et al. |
| 2003/0058111 | A1 * | 3/2003 | Lee et al. ............ 340/573.1 |
| 2003/0118974 | A1 * | 6/2003 | Obrador ................. 434/236 |
| 2003/0142041 | A1 | 7/2003 | Barlow et al. |
| 2003/0210255 | A1 | 11/2003 | Hiraki |
| 2004/0019503 | A1 * | 1/2004 | Berenguer ................. 705/2 |
| 2005/0137648 | A1 * | 6/2005 | Cosendai et al. ........... 607/48 |

FOREIGN PATENT DOCUMENTS

| | | |
|---|---|---|
| EP | 1 220 530 A2 | 7/2002 |
| WO | WO 01/26021 | 4/2001 |
| WO | WO 01/71636 | 9/2001 |
| WO | WO 02/27640 | 4/2002 |

OTHER PUBLICATIONS

Olivier Liechti et al., "A Digital Photography Framework Enabling Affective Awareness in Home Communication".

Rebecca Hansson et al., "The LoveBomb: Encouraging the Communication of Emotions in Public Spaces", Interactive Institute, Sweden, www.playresearch.com.

Jennifer Healey et al., "StartleCam: A Cybernetic Wearable Camera", Oct. 1998, pp. 1-8, 2nd International Symposium on Wearable Computers 1998.

Don Lake, "How a Cybernetic Camera Triggered by the Subconscious Could Tackle Image Overload", Nov. 2000, pp. 21-23.

Jennifer Healey, "Wearable and Automotive Systems for Affect Recognition from Physiology", May 2000, pp. 1-3, Massachusetts Institute of Technology.

Applied Science Laboratories, "Technology and Systems for Eye Tracking: Model H6", www.a-s-l.com.

"Looking at Pictures:Affective facial, visceral, and behavioral reactions", by Peter J. Lang et al., Psychophysiology, 30 (1993) 261-273.

"FotoFile: A Consumer Multimedia Organization and Retrieval System", by Allan Kuchinsky et al.

"Facial ExpressionRecognition using a Dynamic Model and Motion Energy", by Irfan Essa et al. MIT Media Laboratory Perceptual Computing Section Technical Report No. 307, pp. 1-8.

Digital Still Camera Image File Format Standard, Version 2.1, Jul. 1998, Japan Electronic Industry Development Association.

"Behind Blue Eyes" by Claire Tristram, Technology Review, May 2001.

CompactFlash Specification Revision 1.4, CompactFlash Association, Jul. 1999.

U.S. Appl. No. 09/549,356, entitled "Customizing A Digital Camera" filed Apr. 14, 2000, by Prabu et al.

* cited by examiner

IMAGING METHOD AND SYSTEM FOR HEALTH MONITORING AND PERSONAL SECURITY

CROSS REFERENCE TO RELATED APPLICATIONS

Reference is made to commonly assigned U.S. patent application Ser. No. 09/721,222, entitled "Method For Adding Personalized Metadata To A Collection Of Digital Images" filed by Paruiski et al. on Nov. 22, 2000; Ser. No. 10/036,113, entitled "Method For Creating And Using Affective Information In A Digital Imaging System" filed by Matraszek et al. on Dec. 26, 2001; Ser. No. 10/036,123 entitled "Method For Using Affective Information Recorded With Digital Images For Producing An Album Page" filed by Matraszek et al. on Dec. 26, 2001; Ser. No. 10/304,127, entitled "Imaging Method and Apparatus" filed by Elena A. Fedorovskaya et al. on Nov. 25, 2002; Ser. No. 10/303,978, entitled "Camera System With Eye Monitoring" filed by Miller et al. on Nov. 25, 2002; and Ser. No. 10/303,520, entitled "Method and Computer Program Product For Determining an Area of Importance In An Image Using Eye Monitoring Information" filed by Miller et al. on Nov. 25, 2002, the disclosures of which are incorporated herein by reference.

FIELD OF THE INVENTION

The present invention relates to systems that capture digital images and, more particularly, to systems that capture digital images and associate them with affective information.

BACKGROUND OF THE INVENTION

The external events of everyday life evoke or trigger specific emotional, behavioral, and/or physiological responses in individuals. These responses provide an important source of information for a physician or a therapist in order to identify a problem or dysfunction, and suggest a treatment or develop an individualized therapeutic procedure. Review and analysis of these responses can also help individuals to raise their awareness of response patterns to certain situations so that they can improve their reactions. In fact, various psychological therapies, such as cognitive, behavior, etc., are aimed at identifying and changing habitual reactions and response patterns that may cause an individual to feel anxious, depressed or angry.

Accordingly, the ability to track external events and individual behavioral, emotional and/or physiological responses to those events could be a very useful tool for various health applications. Such a system can also be utilized for personal security purposes, when a particular emotional or physiological reaction can trigger selective transmittance of a signal to alert friends, relatives or a specific agency based on the danger and urgency.

A number of systems are known, which are designed to provide remote monitoring of a person.

The typical structure of such health monitoring systems can be described as containing a sensor part for sensing a biometric signal on a patient being monitored and a patient electronic data collection system to record data that is collected by the sensor. A processing part is also supplied. The processing part analyzes, or compresses, or otherwise processes, the recorded data. A communication part is typically supplied and, which is used to transmit signals wirelessly to a centralized server over a telecommunications network, a medical care provider or a database. Wearable devices with the above properties are disclosed in U.S. Pat. No. 6,287,252, entitled "Patient Monitor" filed on Jun. 30, 1999, by Lugo; U.S. Pub. No. US2002/0019584, entitled "Wireless Internet BioTelemetry Monitoring System And Interface" published on Feb. 14, 2002, by Schulze et al.; WIPO Pub. No. WO 01/26021, entitled "Remote Patient Assessment System" published on Apr. 12, 2001, by Anderson et al.; WIPO Pub. No. WO 01/71636 entitled "Personalized Health Profiling System And Method" published on Sep. 27, 2001, by O'Young; and WIPO Pub. No. WO 02/27640, entitled "System And Method For Wireless Communication Of Sensed Data To A Central Server" published on Apr. 4, 2002, by Whittington et al. In some of these systems additional information is also available, such a patient identifier, authorization for the access to the database, etc.

Other personal portable systems that can be found in the patent literature are primarily designed for security and tracking applications. Thus, a signaling system for rendering an alarm for an individual in distress combined with a locating and tracking system of alert and direct appropriate personnel to the needs of the individual in distress and to monitor location of that individual was disclosed in U.S. Pat. No. 5,742,233, entitled "Personal Security And Tracking System" filed on Apr. 21, 1998, by Hoffman et al. The described system comprises a portable signaling unit, a remote alarm switch device, a central dispatch station, and a wireless communication system such as a cellular or telephone system, etc., and a GPS or similar system. The portable signaling unit and the remote alarm switch may be adapted to be worn at different locations on the person's body. When the wearer activates the remote alarm switch or manual alarm switch in a dangerous situation or when the signaling unit or its alarm switch are removed forcefully, data are transmitted to the central dispatch station, where the user identification, stored personal information, the nature of alarm and location of the wearer are displayed.

A more sophisticated system, which is capable of generating a distress signal, is disclosed in U.S. Pat. No. 6,294,993, entitled "System For Providing Personal Security Via Event Detection" filed on Sep. 25, 2001, by Calaman. In this system, event detection is performed by detecting a wearable sensor that detects changes in physiological signals. One embodiment of the system uses a sensor that detects changes in galvanic skin response which is a change in skin conductivity. The system can also operate in a manual mode: when the user manually initiates the distress signal. When the sensor detects that an emergency situation has arisen, appropriate emergency management services are contacted.

While some of the described apparata record and transmit physiological signals of the user, or manually entered signals of emergency, none of them is capable of additionally registering external events in the form of images or video. Therefore these systems do not allow establishing connections between specific external events and person's reactions to them for the benefit of the user's health and therapy. These types of systems do not permit an independent assessment of the real danger or its causes in security applications, because an external event, which is causing an alarm, remains unknown at the emergency service location.

Various methods are known in the art for deriving affective information based upon a user's reaction to an image. One example of a system that monitors physiological conditions to derive affective information is a wearable capture system that enables the classification of images as important or unimportant based on biosignals from human body. This system was described in an article entitled "Humanistic Intelligence: "WearComp" as a new framework and application for intelligent signal processing" published in the Proceedings of the Institute of Electrical and Electronics Engineers (IEEE), 86, pp. 2123-2151, 1998 by Mann. In his paper, Mann described an example of how the system could potentially operate in a situation when a wearer was attacked by a robber wielding a shotgun, and demanding cash. In this case, the system detects physiological signals such as a sudden increase of the wearer's heart rate with no corresponding increase in footstep rate. Then, the system makes an inference from the biosignals about high importance of the visual information. This, in turn, triggers recording of images from the wearer's camera and sending these images to friends or relatives who would determine a degree of a danger.

Another example of such a system is described in a paper entitled, "StartleCam: A Cybernetic Wearable Camera" published in: Proceedings of the Second International Symposium on Wearable Computers, 1998, by Healey et al. In the system proposed in this paper, a wearable video camera with a computer and a physiological sensor that monitors skin conductivity are used. The system is based on detecting a startle response—a fast change in the skin conductance. Such a change in the skin conductance is often associated with reactions of sudden arousal, fear or stress. When the startle response is detected, a buffer of digital images, recently captured by the wearer's digital camera, is saved and can be optionally transmitted wirelessly to the remote computer. By setting a high threshold for the startle detector, the device will record only the most arousing or threatening events. This mode of operation would be most useful for a safety application in which images of the threatening events are transmitted to secure websites of the wearer's "safety net" of friends and family. In another mode, the camera can be set to automatically record images at, a specified frequency, when very few responses have been detected from the wearer, indicating that their attention level has dropped. This mode can be useful at a meeting or a lecture. Such selective storage of digital images creates a "memory" archive for the wearer which aims to mimic the wearer's own selective memory response.

The systems proposed by Mann, and Healey et al. make use of the physiological signals to classify images as "important" (stressful) (i.e., causing rapid change in a biological response) and "unimportant" (ordinary) (i.e., not causing rapid change in a biological response), and trigger the wearable camera to store and/or transmit only the "important" images. However, their systems have several shortcomings.

The described systems do not associate, do not store, and do not transmit the physiological signals (or any other "importance" identifier) together with the corresponding images. As a result, the "important" images can be easily lost among other images in a database, since there is nothing in "important" images indicates that these images are "important". This can happen, for example, when the digital image files are used on a different system, when the images are transferred via a CD-R or other media, when the images are uploaded to an on-line photo service provider, etc. The described systems also do not associate, do not store, and do not transmit user's identifier together with the corresponding images. Therefore, when the system is used by more that one user, it is unable to distinguish which user reacts to the image as "important" or otherwise significant.

Further, the above described systems provide only binary classification "important-unimportant" or "stressful-ordinary" and do not allow a finer differentiation of the relative degree of importance between the captured images.

Additionally, the described systems provide image classification only based on "importance" attribute. For example, they are unable to differentiate whether the important image evoked a positive (happy) or negative (unhappy) reaction in the user. Therefore, a wide range of human emotional reactions (e.g., joy, sadness, anger, fear, interest, etc.) is not considered in the system and cannot be used for monitoring and analysis purposes.

Although some of the above described systems can be triggered by a physiological signal that is indicative of a specific user's reaction to an event as suggested by the galvanic skin response to store and transmit corresponding images, these systems do not have the capability to be triggered by a pre-specified image characteristics, such as a particular subject matter (i.e. a familiar person), scene type (i.e. indoor-outdoor), etc.

Finally, the above described systems also do not have the means to provide a feedback to the user with respect to certain individual reactions to external events, which may be important for specific health and security-related purposes.

The absence of these characteristics in the above described systems limits the scope of the usefulness with respect to health and security related applications by, for example, preventing a further analysis of a person's reactions toward certain situations at a later time as there is no association with a person's identifier and physiological signals. The process of tracking changes in the reactions to similar situations with time (no triggered capture of specific events), which is beneficial for the therapeutic purposes, is also not supported.

Consequently, an additional need exists for an improved system and method for recording and interpreting user's emotional reactions to a scene at the moment of capture an image of the scene for subsequent association of this affective information with the captured image. A user identifier together with the triggered transfer of captured images associated with the characteristic reactions as well as the user's captured reactions associated with the characteristic images.

SUMMARY OF THE INVENTION

In one aspect of the present invention an image capture method is provided. In accordance with the method, an image of the scene is captured and affective information is collected a capture. The scene image and affective information are transmitted to an image receiver.

In another aspect of present invention in image capture method is provided. In accordance with this method, an image is captured of a scene and affective information is collected at capture. The captured image and the collected affective information are analyzed to determine whether a transmission criterion is met. When the transmission criterion is met, the captured image and the collected affective information are transmitted to an image receiver.

In another aspect of the present invention, a reactive imaging method is provided. In accordance with the method, an image of a scene confronting a user is captured and user identification information is obtained. Affective information is collected at capture. The affective information and the user information are associated with the image. The captured image, affective information and user identification are transmitted to a recipient. A reaction is received from the recipient. The reaction is presented to the user.

In another aspect of present invention, an imaging system is provided having an image capture system adapted to capture an image of a scene and a memory which stores the captured image. A set of sensors is adapted to collect affective signals from the user at capture. A processor is adapted to determine affective information based upon the affective signals and associate affective information with the captured image. A transmitter sends the scene image and the affective information to a receiver.

In another aspect of the present invention, an imaging system is provided having an image capture means for capturing an image of a scene and an affective sensor means for collecting affective information from a user at capture. A transmitting means transmits the scene image and affective information to a receiver.

In a further aspect of the invention, a reactive imaging system provided having at least two imaging devices. Each imaging device has image capture system adapted to capture an image of a scene confronting a user and a memory which stores the scene image. Each imaging device also has a set of sensors adapted to capture affective signals from the user at capture and a processor adapted determine affective information based upon the signals from the set of sensors and to associate of the affective information with the scene image. A transmitter sends the scene image and associated affective information to a receiving mode. The receiving node receives the transmitted image and associate affective information. The receiving node has a processor to analyze the transmitted images and affective information and to determine a reaction based upon the transmitted images and affective information.

DETAILED DESCRIPTION OF THE INVENTION

Figure 1A:
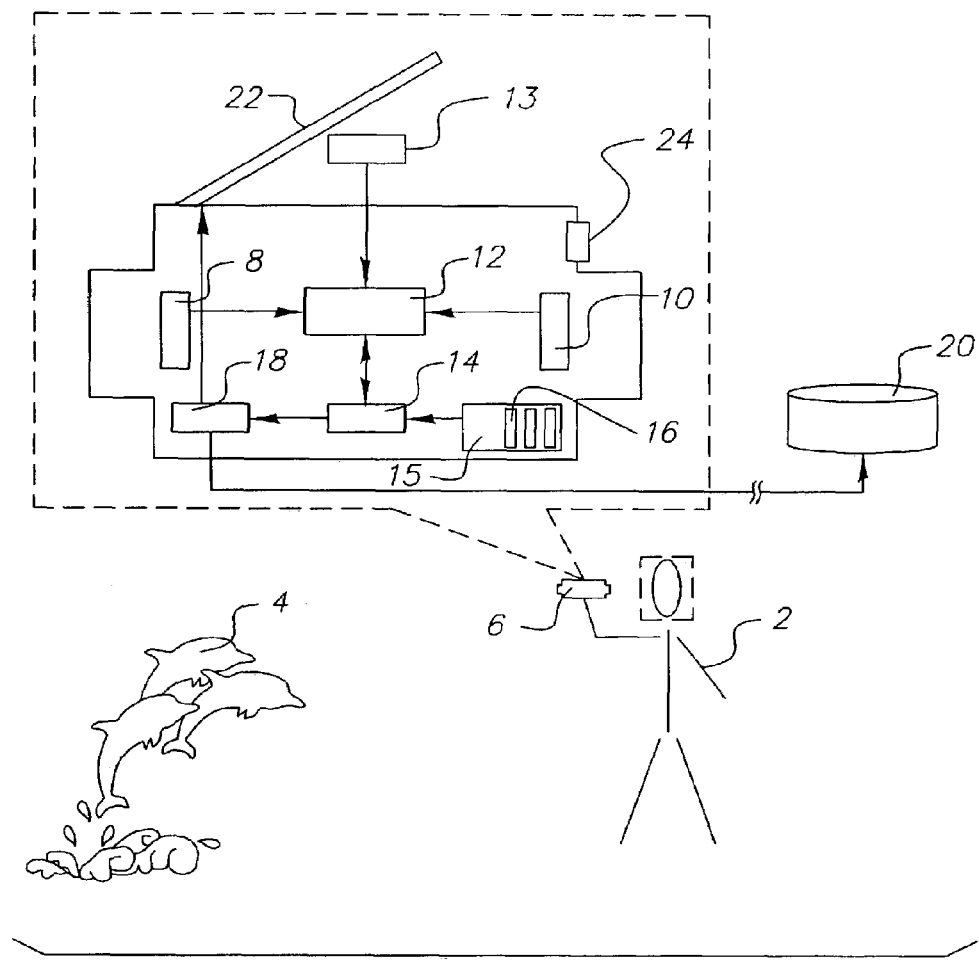
FIG. 1a shows a handheld embodiment of an image capture system in accordance with the present invention.

The present invention provides a method for collecting affective information as a particular user views the scene, associating this information and its interpretation with a captured image of the specified scene for subsequent usage of the affective information and the image together with the information derived from the image. The present invention also provides for collecting and associating available non-image data that is related to the image in a way that is useful for personal health and security applications.

Information that represents user's psychological, physiological, and behavior behavioral reactions to a particular scene or an image of the scene, is referred to herein as affective information. Affective information can include raw physiological and behavioral signals (e.g., galvanic skin response, heart rate, facial expressions, etc.) as well as their psychological interpretation (e.g., preferred, not preferred, etc.), and association with an emotional category (e.g., fear, anger, happiness, etc.). The affective information is changed when a user's psychological reaction is changed. This can happen, for example, when a user suddenly sees a dangerous accident, an amazing action, or a beautiful landscape.

Interpretation of affective information can provide several gradations of user's preference (e.g., the degree to which the user likes or dislikes the scene). It also can provide an indication of the relative degree of importance of the scene to the user. Additionally, interpretation of affective information can be done in terms of the specific emotion (e.g., happiness, sadness, fear, anger, etc.) evoked by the scene.

A scene is defined as something seen by a viewer. It can be referred to as the place where an action or event occurs, an assemblage of objects seen by a viewer, a series of actions and events, landscape or part of a landscape, scenery, etc. Scenes recorded or displayed by an imaging capture device are referred to as images of scenes. Examples of image capture devices include a digital still camera, a handheld video camera, a wearable video camera, a conventional photographic camera that records images such as still or motion picture images on a film, an analog video camera etc. The user can observe scenes directly, through a camera's viewfinder, or on a camera preview screen serving as a viewfinder.

As used herein the terms image and images include but are not limited to still images, motion images, multi-perspective images such a stereo images or other depth images, and other forms of immersive still and motion images.

Information derived from the image of the scene relates to the knowledge about the scene, such as place, type of the place, description or classification of the event, and knowledge about elements of the scene, such as colors, objects, people, etc. that can be extracted from the image of the scene.

Non-image data refers to other types of available information associated with the image. Examples of non-image data associated with the image are a date and time of the moment the image was captured provided by a camera.

People capture images of different scenes for a variety of purposes and applications. Capturing memorable events is one example of an activity that ordinary people, professional photographers, or journalists alike have in common. These events are meaningful or emotionally important to an individual or a group of individuals. Images of such events attract special attention, elicit memories, and evoke emotions, or, in general terms, they produce psychological reactions. Often these psychological reactions are accompanied by physiological and/or behavior changes.

Affective tagging is defined as the process of determining affective information, and storing the affective information in association with images of a particular scene. When the affective information is stored in association with a user identifier, it is referred to herein as "personal affective information". The user identifier can be any type of information that enables a particular user to be identified. The user identifier can be a personal identification code such as a globally unique ID (GUID), user number, social security number, or the like. The user identifier can also be a complete legal name, a nickname, a computer user name, or the like. The user identifier can alternatively include information such as a facial image or description, fingerprint image or description, retina scan, or the like. The user identification can also be an internet address, cellular telephone number or other identification.

When the personal affective information is stored in association with the corresponding image, it is referred to as "personal affective tag". The affective information and user identifier are types of image "metadata", which is a term used for any non-image information relating to an image. Examples of other types of image metadata that can be incorporated in the personal affective information that is stored in the affective tag includes information derived from scene images and non-image data such as image capture time, capture device type, capture location, date of capture, image capture parameters, image editing history etc.

The personal affective information can be associated with a digital image by storing the personal affective information within the image file, for example using a Tagged Image File Format IFD within an Exif image file. Alternatively, the affective information can be stored in one or more application segments in a Joint Photographic Export Group file containing the first image (or alternatively the second image) in accordance with the JPEG standard format ISO 10918-1 (ITU—T.81). This allows a single, industry standard image file to contain both a JPEG compressed first image stored as a normal JPEG image, and the affective information to be stored in a proprietary form that is ignored by normal JPEG readers. In still another alternative, the personal affective information can be stored in a database that is separate from the image. This information can also be stored along with security and access permission information to prevent unauthorized access to the information.

Affective tagging can be done either manually or automatically, as a user views a particular scene or images of the scene using an imaging capture device. In the case of the manual affective tagging, the user might use camera's knobs, touch-screen display, or voice recognition interface to provide his/her reaction to the scene. For example, in the case of a surprise, the user might "click" a camera's button representing "surprise" reaction, or simply say a keyword such as "Wow!".

In the case of automatic affective tagging, an image capture system for personal health and security monitoring (further referred to as simply an image capture system) can use one of the following signals or their combinations to collect affective information for its subsequent interpretation:

Eye movement characteristics (e.g., eye fixation duration, pupil size, blink rate, gaze direction, eye ball acceleration, features and parameters extracted from the eye movement patterns, their complexity, etc.);

Biometric or physiological responses (e.g., galvanic skin response (GSR), hand temperature, heart rate, electromyogram (EMG), breathing patterns, electroencephalogram (EEG), brain-imaging signals, etc.);

Facial expressions (e.g., smile, frowns, etc.);

Vocal characteristics (e.g., loudness, rate, pitch, etc.);

Body gestures including facial movements (e.g., pinching bridge of the nose, rubbing around ears, etc.).

In accordance with one embodiment of this invention described below, affective information is determined automatically based on facial expression, eye fixation duration, and galvanic skin response.

Figure 1B:
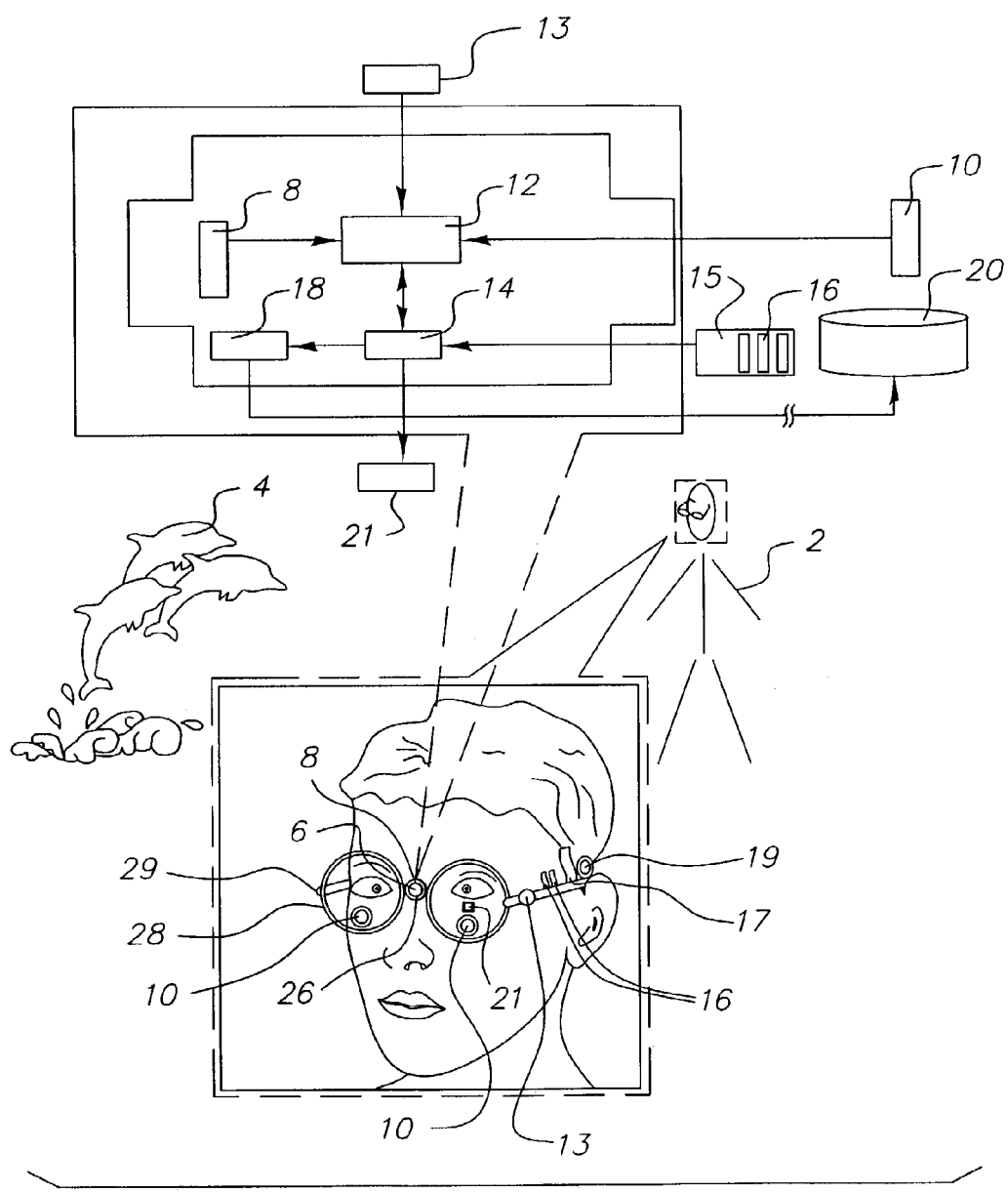
FIG. 1b shows a wearable embodiment of an image capture system in accordance with the present invention.
Figure 1C:
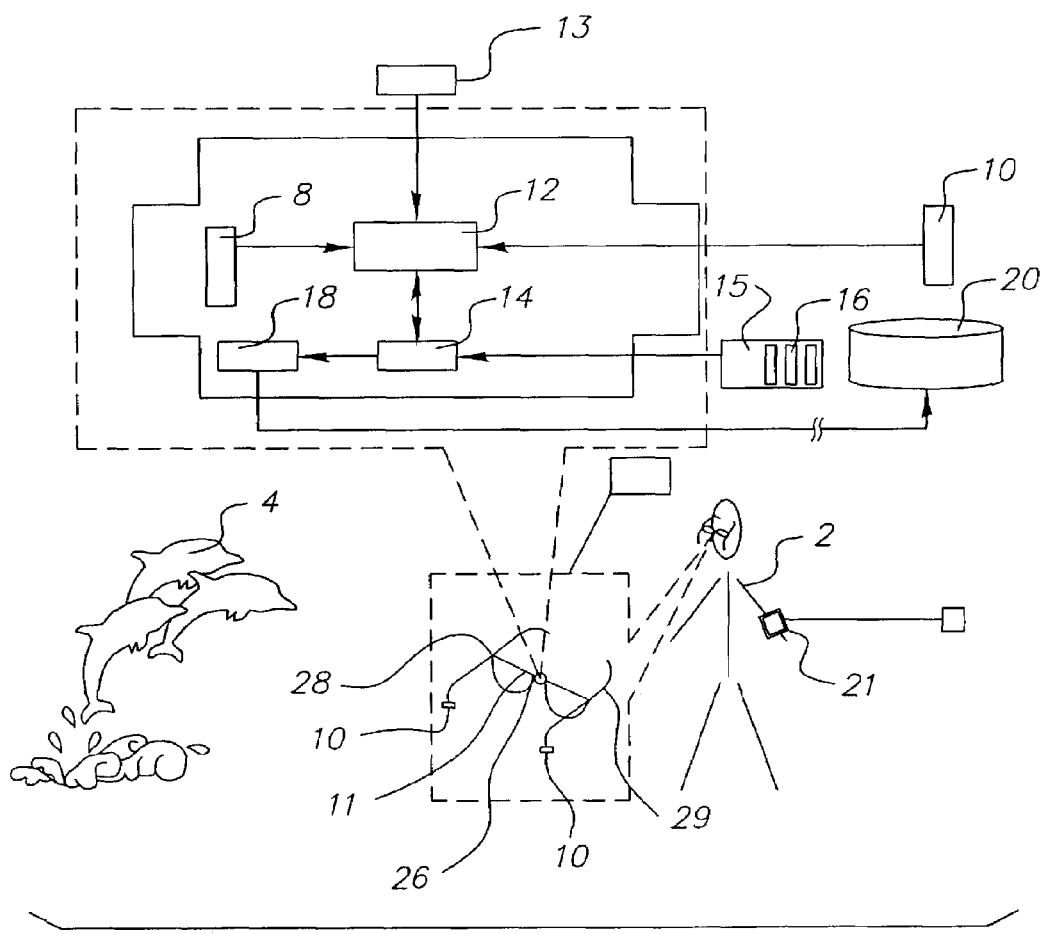
FIG. 1c shows another wearable embodiment of an image capture system of the present invention.

Referring to FIGS. 1a-1c, there are illustrated three example embodiments of image capture systems made in accordance with the present invention. The system depicted in FIG. 1a includes a handheld image capture device 6 in possession of a particular user 2, who views a scene 4 either directly, or through a viewfinder 24, or on a camera preview screen 22, which is also used for communication and a feedback. Image capture device 6 can comprise a digital still camera, handheld digital video camera or a wearable video camera, etc. Examples of wearable embodiments of image capture device 6 are shown in FIG. 1b and FIG. 1c. These wearable embodiments have a display 21 for communication and feedback, either as attached to frame 29 carrying image capture device 6 as depicted in FIG. 1b or as a separate device connected with the image capture device 6 with wires or wirelessly, as depicted in FIG. 1c.

Image capture device 6 includes a capture module 8 to capture images of the scene 4. Capture module 8 includes a taking lens (not shown), an image sensor (not shown) and an A/D converter (not shown). Capture module 8 can also include a microphone (not shown), audio amplifier (not shown), and audio A/D converter (not shown). Capture module 8 provides digital still or motion image signals and associated digital audio signals. Image capture device 6 also includes a central processing unit (CPU) 14 and a digital storage device 12, that can store high-resolution image files such as digital still or digital motion images provided by capture module 8 as well as associated metadata. Digital storage device 12 can be a miniature magnetic hard drive, Flash EPROM memory, or other type of digital memory.

Image capture device 6 is shown having a communication module 18 such as a wireless modem or other communication interface that exchanges data including digital still and video images using a communication service provider, such as an Internet service provider 20. Communication module 18 can use a standard radio frequency wireless interface, such as the well-known Bluetooth interface or the IEEE Standard 802.15 interface. Alternatively, communication module 18 can exchange information with other devices using infra-red, laser, or other optical communication schemes. In still another alternative, image capture device 6 can have a communication module 18 that is adapted to use data exchange hardware such as a Uniform Serial Bus cable, IEEE Standard 1394 cable, other electrical data paths such as a wire, set of wires or waveguide, or an optical data path to permit information including digital images and affective information to be exchanged between image capture device 6 and other devices.

Referring to FIG. 1a the communication module 18 connects to the preview display 22 in order to play messages or provide video communication using a communication service provider 20. In the embodiments shown in FIGS. 1b and 1c, messages and video information received by the user are displayed on a communication display 21 located on a wearable embodiment of image capture system 6. One example of display 21 that could be attached to the glasses frame is a qVGA Invisible Monitor Model EG-7 sold by MicroOptical, Westwood, Mass., USA. FIG. 1c shows another example of display 21 worn on a wrist in a portable communication module 23.

In order to obtain affective information, image capture device 6 includes controls 13 and a set of sensors 15 that can detect physiological signals from user 2. User 2 can enter affective information by using controls 13, which can include, for example, manual control buttons, a touch screen display, a voice recognition interface or a gesture recognition interface.

Affective information can also be gathered by the set of sensors 15. In the embodiment shown in FIG. 1a, the set of sensors 15 includes galvanic skin response sensors 16 that are mounted on the surface of the image capture device 6. In wearable embodiments galvanic skin response sensors 16 could be mounted elsewhere outside the image capture device 6 as shown in FIG. 1b, where galvanic skin response sensors 16 are located on the sidepiece 29 of a conventional frame 28 used for supporting glasses. The set of sensors 15 can also include a vascular sensor 17, usefully incorporated on a portion of the sidepiece 29 proximate to the arteries in the temple of the head of the user thus facilitating measurement of temperature and/or heart rate readings. The set of sensors 15 can also include a vibration sensor 19 as is depicted in FIG. 1b proximate to the ears and can be adapted to detect audible vibration proximate to the ear or by way of contact with the ear. Vibration sensor 19 can be adapted to detect both sounds emanating from the user and sounds that emanate from other sources. Any of the set of sensors 15 can be located in other useful arrangements. Any one of the set of sensors 15 can be miniaturized so that their presence would not alter the appearance of a wearable embodiment of image capture device 6. For example, as is shown in the embodiment of FIG. 1c sensors 16 for detecting galvanic skin response are a part of a wearable image capture device 6 mounted on a bridge 26 of a conventional frame 28.

In other embodiments, the sensors 15 can comprise neural sensors and other devices adapted to monitor electrical activity from nerve cells to allow for interaction with the environment. Examples of such a device have been proposed as the brain communicator and the Muscle Communicator sold by Neural Signals, Inc., Atlanta Ga., U.S.A. These devices monitor, respectively, electrical signals at a nerve cell and signals radiated by certain nerves to detect the signals that are used for example to cause an average person to move an extremity. These signals are transmitted to a computer, where software decodes the signals into useful information. It will be appreciated that such technology can be used to detect affective information as well as other information useful in determining affective information. For example, neural activity along a nerve carrying sound information from an ear can be monitored and used to determine audio information that reflects what the observer actually heard at an event.

Image capture device 6 also includes a user video camera 10, which is used to record video images of eye movements, pupil size, and facial expressions of the user 2. User video camera 10 can incorporate for example a conventional charge couple device imager, a complimentary metal oxide imager or a charge injection device. Other imaging technologies can also be used. The images that are captured by user video camera 10 can include video images for forming an image of the user or some feature of the user's face. The images that are captured by user video camera 10 can also include other forms of video images from which affective information can be obtained. For example, images that represent eye position and pupil size do not need to constitute full digital images of an eye of user 2. Instead other forms of imaging can be used that have lower resolution or a non-linear imaging pattern in order to reduce costs or to simplify the imaging structure.

The video images captured by user video camera 10 are stored on the digital storage device 12 prior to processing by the CPU 14. User video camera 10 can include, for example, an infrared sensitive camera. In this embodiment, a set of infrared light emitting diodes (infrared LEDs) direct infrared light toward the pupils of user. User video camera 10 detects infrared signals radiated by the eyes of the user. The pupils are then are tracked from the facial image of the user. One example of a useful user video camera 10 is the Blue Eyes camera sold by International Business Machines, Armonk, N.Y., U.S.A. Another useful example of user video camera 10 is the Eyegaze System sold by LC Technologies, Inc., Fairfax, Va., U.S.A.

Other useful embodiments of user video camera 10 are shown and described in greater detail in commonly assigned U.S. application Ser. No. 10/303.978 (Our Docket # 85243 entitled "Camera System With Eye Monitoring".)

User video camera 10 can be attached to or located inside of the handheld image capture device 6 such as shown in FIG. 1a, on a glasses frame 28 such as is shown with the wearable image capture device 6 of FIG. 1b, or on a remote portion of glasses frame 28 such as is shown with wearable image capture device 6 as shown in FIG. 1c. In the case of FIG. 1c, user video camera 10 is especially suitable for capturing a variety of facial features of the user, including pupil size, eye and brow movements. In the case depicted on FIG. 1b, it is best suited for capturing eye movements and other eye characteristics. User video camera 10 can also be separate from image capture device 6, and in this embodiment user video camera 10 can comprise any image capture device that can capture an image of user of image capture device 6 and transfer this image to the image capture device 6. The transfer of images from a remote user video camera 10 can be done wirelessly using any known wireless communication system.

Feature tracking can performed using various algorithms, such as for example, described in an article entitled "Facial Feature Tracking for Eye-Head Controlled Human Computer Interface", published in Proceedings of IEEE TEN-CON, 1999, pp. 72-75 by Ko et al. This algorithm, capable of real-time facial feature tracking, composes complete graph using candidate blocks it identifies from a processed facial image, and then computes a measure of similarity for each pair of blocks. The eyes are located as the blocks having the maximum similarity. Based on the eye position, the mouth, lip-corners and nostrils are located. The located features are then tracked.

One example of a wearable image capture device 6 having an user video camera 10 that is adapted to record eye movements can be found, for example, in "Oculomotor Behavior and Perceptual Strategies in Complex Tasks" by Pelz et al. In: Vision Research, 41, pp. 3587-3596, [2001]. The authors describe a wearable lightweight eye tracking system in the form of a head-gear/goggles, which include a module containing an infrared illuminator, a miniature video eye camera, and a beam-splitter to align the camera to be coaxial with the illuminating beam. Retro-reflection provides the pupil illumination to produce a bright-pupil image. An external mirror folds the optical path toward the front of the goggles, where a hot mirror directs the infrared illumination toward the eye and reflects the eye image back to the eye camera. A second miniature camera is mounted on the goggles to capture a scene image from the user's perspective.

In both FIG. 1b and FIG. 1c user video camera 10 consists of two pieces, which enable capture of eye characteristics of both eyes. It is, however, understood that user video camera 10 may be represented by one piece that captures the eye characteristics of both or only one of the eyes of user 2.

Image capture device 6 is provided with appropriate software which is utilized by CPU 14 for creating and using personalized affective information. This software is typically stored on digital storage device 12, and can be uploaded or updated using communication module 18. In addition, software programs to enable CPU 14 to perform image processing and analysis pertaining to non-affective information, which can be extracted from images of the scene provided by capture module 8, are also stored on the digital storage device 12. The digital storage device 12 can also store information with respect to a personal user profile, which could be a specific database that includes information summarizing characteristics reactions of user 2 such as, for example, quantitative information about typical reaction patterns to certain scenes or situations as well as a software program to enable CPU 14 to access this specific database when creating and using personalized affective information. This quantitative information can comprise, for example, cumulative distribution of user's reaction to scenes or situations and that characterize, for example, a user's degree of preference for these scenes or situations. This personal user profile can be queried by CPU 14. The personal user profile is also updated by new information that is learned about the reactions of user 2.

It is understood that all parts and components of image capture device 6 discussed above may be implemented as integral parts of the image capture device 6 or as physically separate devices connected with wires or wirelessly.

The following describes various embodiments of methods for image capture device 6 to determine affective information based on analysis of facial characteristics such as: a degree of preference extracted from facial expression, or an emotion category and its distinctiveness extracted from a facial expression. Other embodiments show methods for determining affective information based upon physiological information such as a degree of interest extracted from pupil size and eye movements or a degree of excitement extracted from galvanic skin response. Further embodiments show methods for using a combination of emotion category and a degree of excitement to determine affective information. Depending on the application a particular embodiment might be chosen. For example, determining affective information based on the degree of preference could be very useful for positive therapy, where one of the goals is to facilitate and promote positive experiences. At the same time for security applications and other types of therapy detecting events evocative of negative emotions is important.

Figure 2A:
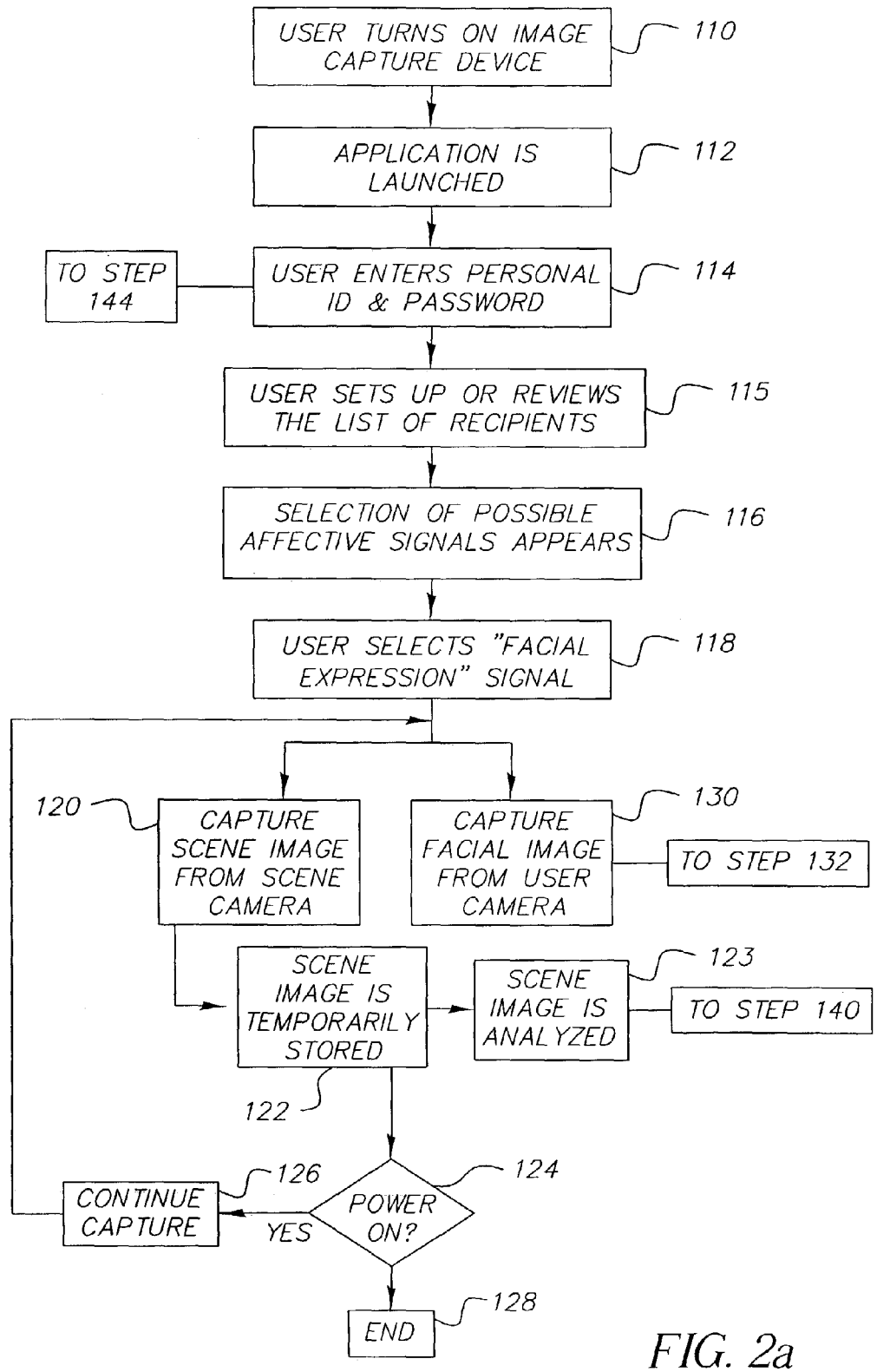
FIGS. 2a-2b comprise a flow diagram showing one embodiment of the invention where affective information is provided based on analysis of facial expressions.
Figure 2B:
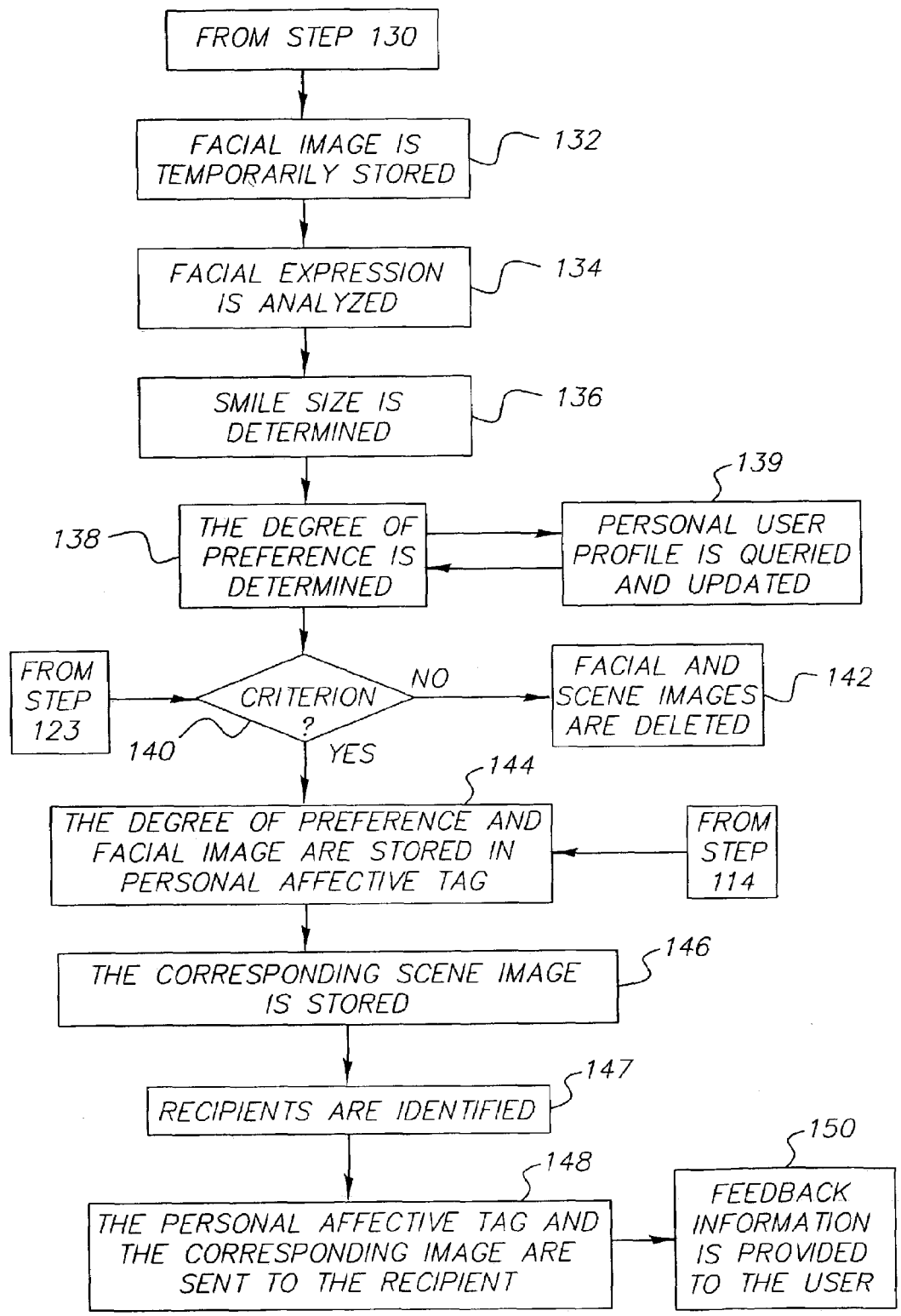

Referring to FIGS. 2a-2b, there is shown a flow diagram illustrating an embodiment of a method of the present invention for providing affective information based on the degree of preference of a particular user for an image of a particular scene. In this embodiment, affective information is determined based on facial expression of the particular user.

User 2 first activates the image capture device 6 (step 110). In one embodiment, the software application that implements the method of the present invention is already installed in the image capture device 6 and it is launched automatically in step 112. Alternatively, user 2 can start the application manually, by using appropriate control buttons (not shown) on the image capture device 6.

User 2 enters a personal ID and password (step 114). In an alternative embodiment, user video camera 10 is used in conjunction with face recognition software to automatically determine the identity of the user, and to provide an appropriate user identifier, such as the user's name or personal identification code or other identification. In another alternative embodiment user identification data can be obtained from data sources that are external such as a radio frequency transponder to capture device 6 using, for example, communication module 18. In a further alternative embodiment, image capture device 6 is pre-programmed with a particular user identifier and step 114 is not required.

User 2 determines a list of recipients to who image capture device 6 will use to send images and affective information and non-affective information (step 115). Following is an example of a possible list of categories of recipients in the order of frequency of communication:
1) a personal database;
2) a family member;
3) a proxy contact;
4) a health care provider;
5) a security agency; and/or
6) a local or regional emergency services system.

Such a list also reflects a level of emergency in the numeration: the larger the number the higher the emergency level. This information is used by the communication module 18 depicted in FIGS. 1a-1c.

Image capture device 6 optionally provides a selection of signals that can be recorded in order to determine the emotional reaction of user 2 as user 2 views a scene (step 116). User 2 selects the desirable signal, i.e., facial expression in this case (step 118). In an alternative embodiment, the image capture device 6 is preprogrammed to use one or more affective signals, and steps 116 and 118 are not required.

User 2 then directs imaging device 6 to compose the scene to be captured. The capture module 8 captures the first image of a scene (step 120) and, simultaneously, in step 130, user camera 10 captures the first facial image of user 2.

Image capture device 6 temporarily stores the scene image (step 122) and automatically analyzes the scene image in various respects (step 123). The goal of such analysis can be to detect a particular subject matter in a scene, which, for example, is known to evoke certain habitual reaction of the user, or to present a threat to the user. Such image analysis can be done using various existing image processing and image understanding algorithms. One such algorithm is disclosed in commonly assigned U.S. Pat. No. 6,282,317 entitled "Strong Signal Cancellation To Enhance Processing Of Weal Spread Spectrum Signal" filed Dec. 14, 1999, by Norman et al. the disclosure of which is incorporated herein by reference, describes a method for automatic determination of main subjects in photographic images by identifying flesh, face, sky, grass, etc. as the semantic saliency features together with the "structural" saliency features related to color, texture, brightness, etc., and then combining those features to generate belief maps. Another image processing technique disclosed in commonly assigned U.S. Pat. Pub. No. US 2002/0076100 A1 entitled "Image Processing Method For Detecting Human Figures In A Digital Image" filed Dec. 14, 2000, by Luo the disclosure of which is incorporated herein by reference, allows detecting human figures in a digital color image. The algorithm first performs a segmentation of the image into non-overlapping regions of homogeneous color or texture, with subsequent detection of candidate regions of human skin color and candidate regions of human faces; and then for each candidate face region, constructs a human figure by grouping regions in the vicinity of the face region according to a pre-defined graphical model of the human figure, giving priority to human skin color regions. The presence of people in a scene or particular people, established using facial recognition algorithms such as described in an article entitled "Face Recognition Using Kernel Based Fisher Discriminant Analysis", published in Proceedings of the Fifth IEEE International Conference on Automatic Face and Gesture Recognition, pp. 0197-0201 (2002) by Liu et al., may also be used.

With respect to the captured facial image described in step 130, the image capture device 6 temporarily stores the facial image in step 132, and automatically analyses the facial expression of user 2 in step 134. Facial expressions can be analyzed using a publicly disclosed algorithm for facial expression recognition such as an algorithm described in an article entitled "Facial Expression Recognition using a Dynamic Model and Motion Energy" published in Proceedings of the ICCV 95, by Essa et al. 1995 Cambridge, Mass. This algorithm is based on knowledge of the probability distribution of the facial muscle activation associated with each expression and a detailed physical model of the skin and muscles. This physics-based model is used to recognize facial expressions through comparison of estimated muscle activations from the video signal and typical muscle activations obtained from a video database of emotional expressions.

Facial expressions can also be analyzed by means of other publicly available algorithms. One example of such an algorithm is found in "Detection, Tracking, and Classification of Action Units in Facial Expression," published in Robotics and Autonomous Systems, 31, pp. 131-146, 2000 by Lien et al. Another similar algorithm is found in an article entitled "Measuring facial expressions by computer image analysis", published in Psychophysiology, 36, pp. 253-263 [1999] by Bartlett et al. These algorithms are based on recognizing specific facial actions—the basic muscle movements—which were described in a paper entitled "Facial Action Coding System", published in Consulting Psychologists Press, Inc., Palo Alto, Calif. [1978] by Ekman et al. In the Facial Action Coding System (FACS), the basic facial actions can be combined to represent any facial expressions. For example, a spontaneous smile can be represented by two basic facial actions: 1) the corners of the mouth are lifted up by a muscle called zygomaticus major; and 2) the eyes are crinkled by a muscle called orbicularis oculi. Therefore, when uplifted mouth and crinkled eyes are detected in the video signal, it means that a person is smiling. As a result of the facial expression analysis, the face of user 2 can be recognized as smiling when a smile is detected on the face of user 2, or not smiling when the smile is not detected.

Image capture device 6 determines the smile size (step 138). If the smile is not detected, the smile size equals 0. If a smile has been detected for a given image, a smile size for this image is determined as the maximum distance between mouth corners within first three seconds after the onset of the specified image divided by the distance between the eyes of user 2. The distance between the person's eyes is determined using the facial recognition algorithms mentioned above. The necessity of taking the ratio between the size of the mouth and some measure related to the head of the person (e.g. the distance between the eyes) stems from the fact that the size of the mouth of user 2 is extracted from the facial images depends on the distance of the user to the video camera, position of the head, etc. The distance between the eyes of user 2 is used to account for this dependency, however, other measures such as the height or width of the face, the area of the face and others measures can also be used.

Image capture device 6 determines the degree of preference (step 138). If the smile was not detected, then the smile size and consequently the degree of preference is equal to 0. If the smile was indeed detected, the absolute degree of preference corresponds to the smile size. The relative degree of preference is defined as the smile size divided by the average smile size for user 2. The average smile size can be constantly updated and stored on digital storage device 12 as a part of a personal user profile for user 2. The personal user profile is queried and updated with respect to the average smile size using the smile size data (step 139).

The obtained degree of preference is compared to a criterion (step 140). The criterion is constructed to reflect the significance of both affective information and image information extracted in steps 123 and 138. Such criterion can be defined for example in the form of the logical "OR" expression. That is if the relevant information in the scene image is detected, or a threshold value for the affective information, namely the degree of preference in the case of FIG. 2, is exceeded, or both a detection of the relevant scene image information and surpassing the threshold for the degree of preference took place, the criterion in the step 140 is met. It is also understood that the criterion in step 140 can be set to give a priority to either of the two sources of information.

In one embodiment the criterion may reflect only the significance of affective information, namely the degree of preference. In this embodiment, the obtained degree of preference is compared to a threshold value established by user 2 or for user 2. If the obtained degree of preference is above the threshold value, image capture device 6 creates a personal affective tag for the corresponding image which indicates a preference for this particular captured image (step 144).

In another embodiment the threshold value for the degree of preference could also be established automatically from the personal user profile, for example, on the basis of the prior cumulative probabilities for the user's degrees of preference distribution. Such probability could be equal to 0.5, and thus, the threshold value for the degree of preference would correspond to the value that occurs in at least 50% of the cases. Alternatively, the personal affective tag can include a value selected from a range of preference values, enabling the differentiation of the relative degree of preference between various captured images.

If the criterion is met, image capture device 6 stores the corresponding image and the personal affective tag, which indicates the degree of preference, within the image file containing the scene image, as part of the image metadata (step 146). Alternatively, the personal affective tag which indicates the degree of preference, can be stored in a separate file in association with the user identifier and the image identifier. In addition, the information about the date that user 2 views a certain image (i.e. immediately upon capture) also can be recorded as a separate entry into the personal affective tag.

In another embodiment the raw facial images are stored as affective information either in a separate file on the image capture device 6 together with the image identifier and the user identifier, or in the personal affective tag as part of the image metadata, and the analysis is done at a later time and optionally using a separate system. For example, the scene image and raw facial image can be communicated using communication module 18 (see FIG. 1) and the Internet Service Provider 20 to a separate desktop computer (not shown) or computer server (not shown), which can perform the analysis described earlier in relation to steps 134-138.

The recipient is identified (step 147). In one embodiment, it can be a personal database, with the e-mail address supplied by Internet Service Provider. In another embodiment the recipient can be a health care provider, or a security agency. In another embodiment, there could be the multiple recipients from the list including a personal database, a health care provider, friends, family members, security agency, etc. The recipients can also be automatically chosen based on the analysis of affective information, image data and non-image data. In this case, such determination as part of the step 147 can consist of, for example, comparing the value for affective information, such as the degree of preference determined in step 138 with the pre-specified thresholds corresponding to each of the recipients from the list of recipients. In yet another embodiment the threshold values for the degree of preference corresponding to each of the recipients is established automatically from the personal user profile, for example, on the basis of the prior cumulative probabilities for the user's degrees of preference distribution. In one embodiment a cumulative probability of 0.9, could be chosen for a health care provider and thus, the threshold value for the degree of preference would correspond to the value that is exceeded in only 10% of the cases. In yet another embodiment, the personal affective tag can include a value selected from a range of preference values, enabling the differentiation of the relative degree of preference between various captured images. In still another embodiment the recipients can be chosen based on solely the results of the scene image analysis or a combination of the scene information and affective information depending on the criterion construction in the step 140.

The corresponding image, the personal affective tag and other image metadata are sent using the communication module 18 for example by way of an Internet Service Provider 20 to the identified recipient, e.g. a personal database of digital images (step 148). This personal database of images can be stored, for example, using separate desktop computer (not shown) or computer server (not shown).

In another embodiment, the corresponding image, the personal affective tag, image metadata including derived image information are sent to a physician or other health care provider for additional analysis of a particular affective reaction of the user to a specific situation or a review. The corresponding image, the personal affective tag, the image metadata and derived information can also be sent to a member of a support network, including family members or local emergency services.

Feedback information is displayed on the camera preview screen 22 or communication display 21 (step 150). This information is automatically generated by the appropriate software program and may contain an image of the scene, the determined degree of preference, or both. It may also include or solely consist of a sound signal, pre-recorded voice message or computer generated speech or images. In another embodiment, a feedback can be sent by a physician or a member of the support network to facilitate therapy or otherwise assist user 2. In this regard, an interactive communication exchange can be initiated.

If the obtained degree of preference is below the threshold value, the facial image of the user and the scene image are deleted (step 242). If the obtained degree of preference is below the threshold value and if user 2 is still viewing the same scene or captured image of the scene, such as for example on preview screen 22, image capture device 6 can optionally capture the next facial image and repeat steps 132 through 140 to determine if user 2 has changed her facial expressions as user 2 views the scene or a captured image of the scene.

If the threshold value is set to 0, all scene images and corresponding affective information (degree of preference or in another embodiment, raw facial image) recorded by the image capture device 6 will be permanently stored as affective information either in a separate file on the image capture device 6 together with the image identifier and the user identifier, or in the personal affective tag as part of the image metadata.

If the user keeps the power turned on, the process of capturing and analyzing the next image of the scene (steps 120-123) and simultaneously determining and storing a personal affective tag for the captured image (steps 130-146) are repeated (step 126).

Image capture device 6 continues recording images of the scene 4 using capture module 8 and facial images of the user 2 using user video camera 10, as long as the user 2 keeps the image capture device 6 powered on (step 126). If the power is turned off, the image capture device 6 stops recording the images of the scene and the facial images and also ends the process of affective tagging (step 128).

The degree of preference can be used in a digital imaging system to rank images in a systematic and continuous manner as favorite images for a specified user as described in commonly assigned U.S. patent application Ser. No. 10/036,113, entitled "Method for Creating and Using Affective Information in a Digital Imaging System" filed Dec. 26, 2001, by Matraszek et al. and in commonly assigned U.S. patent application Ser. No. 10/036,123, entitled "Method for Using Affective Information Recorded With Digital Images for Producing an Album Page" filed Dec. 26, 2001, by Matraszek et al., the disclosures of which are incorporated herein by reference.

The degree of preference for images of a scene can be determined in a binary fashion. When the smile is detected in step 136, the corresponding image is then classified as preferred with the binary degree of preference equals 1. Alternatively, when the smile is not detected, the image is classified as not preferred with the degree of preference equals 0.

The determined affective information in terms of the binary degree of preference is then stored as a personal affective tag, which includes the user identifier as part of the image metadata. It can also be stored in a separate file on digital storage device 12 together with the image identifier and the user identifier. In addition, affective information in terms of the actual image(s) of the user's facial expression can also be stored in a separate file in association with the image identifier and the user identifier.

In another embodiment, captured images are transferred by image capture device 6 to the Internet Service Provider 20 only when the affective information exceeds a threshold, such as a threshold for the relative smile size. As a result, only images, which exceed a preference threshold, are stored in the user's personal database of images. In this embodiment, metadata is stored in the image files that indicate that such files met the threshold.

Figure 3A:
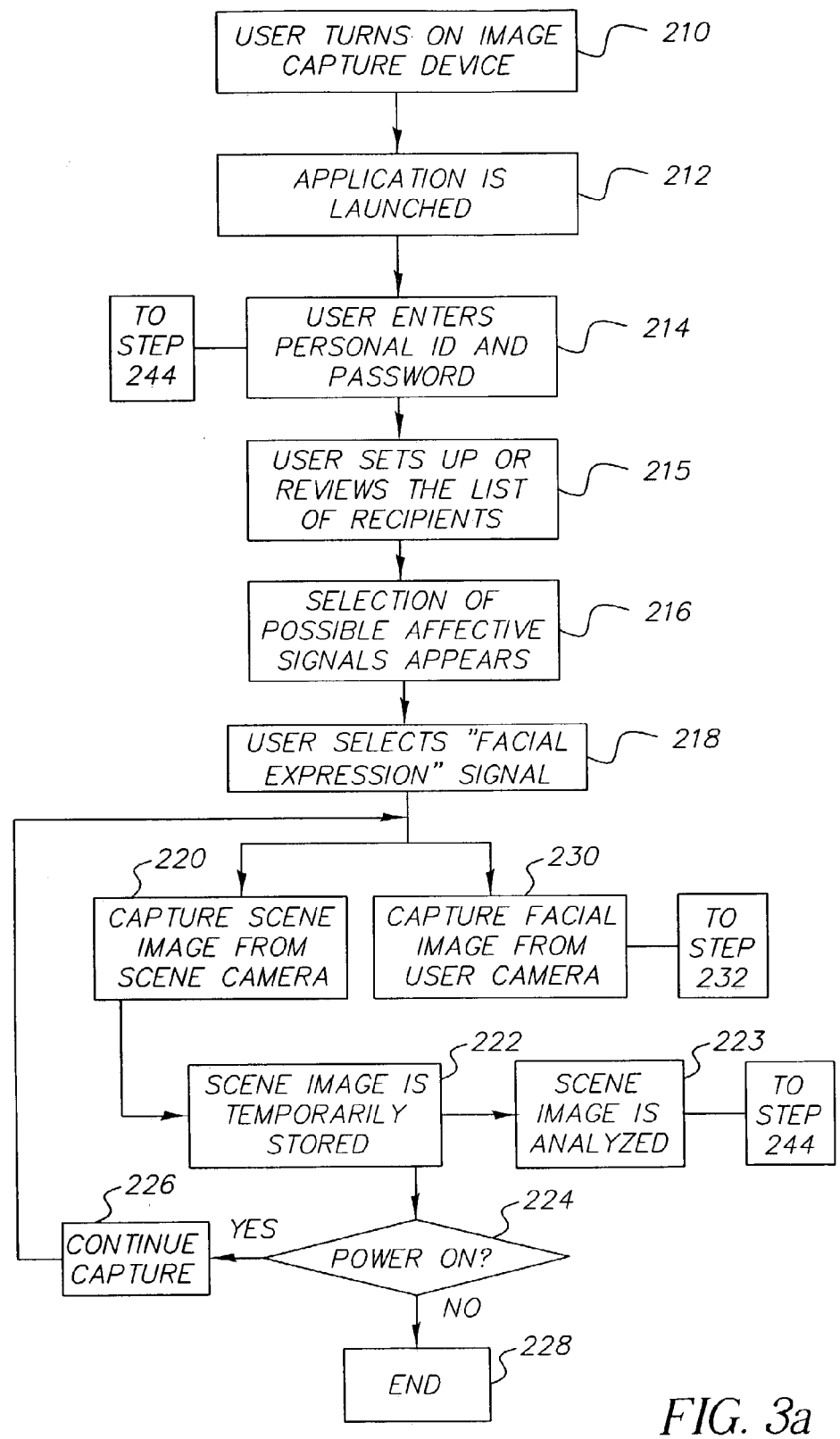
FIGS. 3a-3b comprise a flow diagram showing an embodiment of the invention where affective information is provided based on analysis of facial expressions.
Figure 3B:
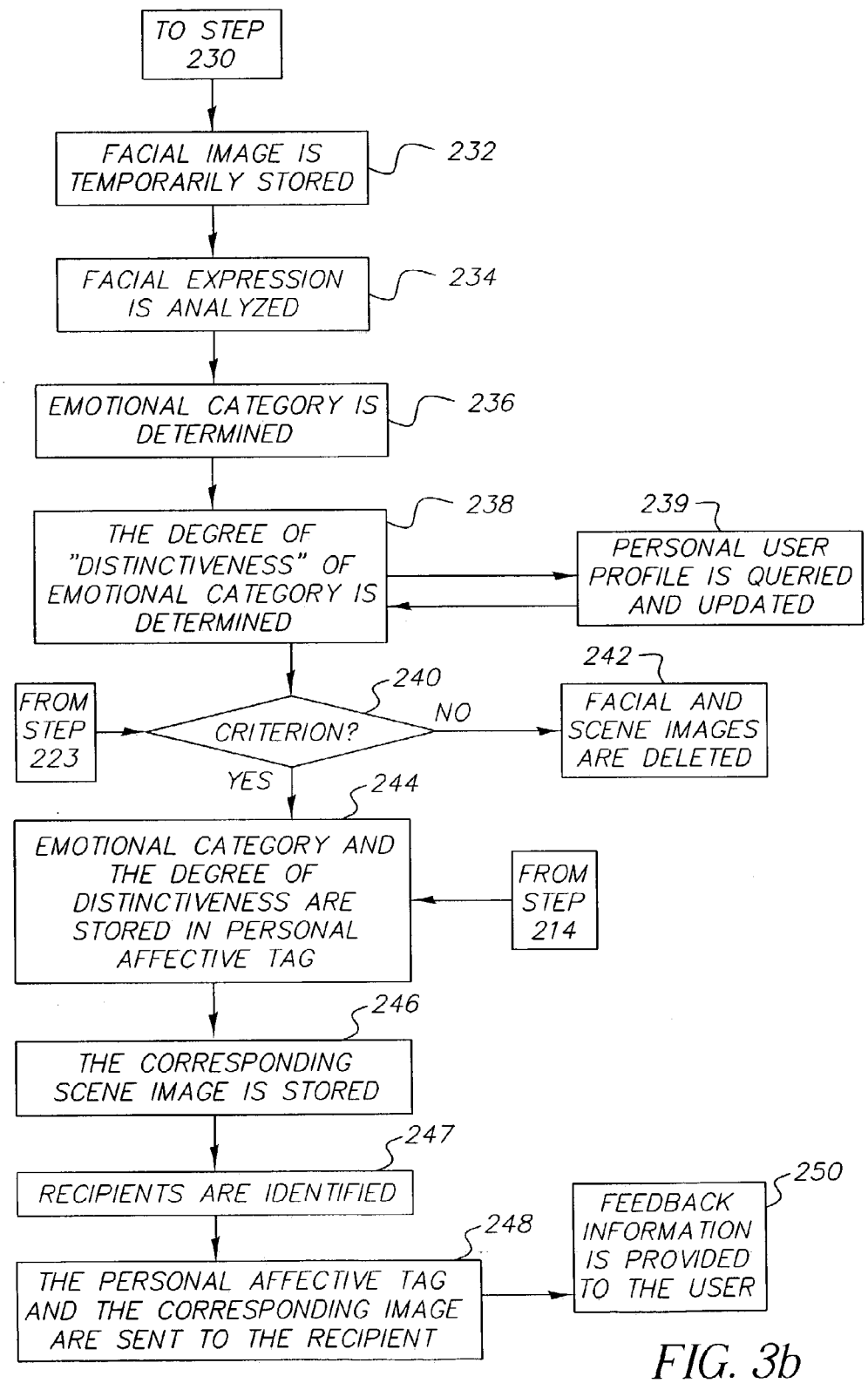

Referring to FIGS. 3*a*-3*b* there is shown a flow diagram illustrating another embodiment of the present invention. In this embodiment, affective information is determined based upon the emotional category of the user's reaction, which corresponds to the captured image. In this embodiment, affective information is also obtained based on the analysis of a user's facial expressions.

Facial expressions may be classified into a broader range of emotional categories, such as 'happiness', 'sadness', 'disgust', 'surprise', etc. A publicly disclosed algorithm that categorizes facial expressions is described in an article entitled "EMPATH: A Neural Network that Categorizes Facial Expressions", published in the Journal of Cognitive Neuroscience, 2002 by Dailey et al. The algorithm classifies facial expressions into six basic emotional categories: 'happy', 'sad', 'afraid', 'angry', 'disgusted', and 'surprised' based on developing a feedforward neural network consisting of three neuron layers performing three levels of processing: perceptual analysis, object representation, and categorization. In the model the first layer mimics a set of neurons with the properties similar to those of complex cells in the visual cortex. The units in the second layer extract regularities from the data. The outputs of the third layer are categorized into six basic emotions. As a result each facial expression will coded by six numbers, one for each emotion. The numbers, corresponding to different emotions are all positive and sum to 1, so they can be interpreted as probabilities.

The following method determines an emotional category based on a user's facial expression, and further provides a range of values for these categories, more specifically, the degree of "distinctiveness" of an emotional category is suggested and shown in FIG. 3. The degree of distinctiveness of an emotional category reflects a measure of uniqueness or "purity" of a particular emotion as opposed to fuzziness or ambiguity of the emotion. In common language such an emotion is often referred to as "mixed feelings". This "uniqueness" characteristic could be thought as somewhat analogous to color saturation.

Steps 210 through 232 of the embodiment of FIGS. 3a-3b, generally correspond to steps 110 through 132 of the embodiment of FIGS. 2a-2b.

However, in this embodiment, image capture device 6 automatically analyzes the facial expression of user 2 applying the neural network method by Dailey et al. which was described previously (step 234). As a result, a facial expression of user 2 is associated with six numbers, one for every basic emotion.

An emotional category (EC) is determined by choosing the category with the largest number (step 236). For example, if the numbers were 0.5, 0.01, 0.2, 0.1, 0.19 and 0 for 'happy', 'sad', 'afraid', 'angry', 'disgusted', and 'surprised', respectively, then the determined emotional category is happy, because it has the largest respective number 0.5. Consequently, scenes that evoke 'happy' facial expressions are assigned the 'happy' emotional category; scenes that evoke 'sad' facial expressions are assigned the 'sad' emotional category, etc. Where several categories have the same number, one category is randomly selected to be to the facial expression. Alternatively, where several categories have the same number additional affective or non-affective information can be used to help select a category.

Image capture device 6 determines the degree of distinctiveness of the emotional category (step 238). The degree of distinctiveness ($DD_{EC}$) is computed from the numbers for six emotions established in the previous step 236, which are denoted for the convenience as N1, N2, N3, N4, N5, and N6. The following expression is used in the present invention for determining the degree of distinctiveness for the identified emotional category EC:

$$DD_{EC} = \sqrt{(N1^2 + N2^2 + N3^2 + N4^2 + N5^2 + N6^2)}$$

$DD_{EC}$ corresponds to the absolute degree of distinctiveness for the emotional category EC. The relative degree of distinctiveness is defined as the absolute degree of distinctiveness for the emotional category EC divided by the average value for the $DD_{EC}$ established for the respective emotional category for the particular user. The average $DD_{EC}$ can be constantly updated and stored on digital storage device 12 as a part of a personal user profile for user 2. The personal user profile is queried and updated with respect to the overage degree of distinctiveness of the emotional category $DD_{EC}$ (step 239).

The obtained degree of distinctiveness is compared to a criterion similarly to the previously explained method of FIG. 2, when the degree of preference was used (step 240). In step 240, the obtained degree of distinctiveness is compared to a criterion, which is constructed to reflect the significance of both image information and affective information extracted in steps 223 and 238. Such criterion can be defined, for example, in the form of the logical "OR" expression. That is, if the relevant information in the scene image is detected, or a threshold value for the affective information, namely the degree of distinctiveness, is exceeded, or both a detection of the relevant scene image information and surpassing the threshold for the degree of distinctiveness took place, the criterion in the step 240 is met. It is also understood that the criterion in step 240 can be set to give a priority to either of the two sources of information.

In one embodiment the criterion may reflect only the significance of affective information, namely the degree of distinctiveness. In such an embodiment, the obtained degree of distinctiveness is compared to a threshold value established by user 2 or for user 2. If the obtained degree of distinctiveness is above the threshold value, then the image capture device 6 creates a personal affective tag for the corresponding image which indicates an emotional category with the degree of its distinctiveness for this particular captured image (step 244).

In another embodiment the threshold value for the degree of distinctiveness could also be established automatically from the personal user profile, for example, on the basis of the prior cumulative probabilities for the user's degrees of distinctiveness distribution for user 2 corresponding to a particular emotional category. Such probability could be equal to 0.5, and thus, the threshold value for the degree of distinctiveness would correspond to the value that occurs in at least 50% of the cases. Alternatively, the personal affective tag can include a value selected from a range of distinctiveness values, enabling the differentiation of the relative degree of distinctiveness between various captured images.

Image capture device 6 stores the corresponding image and the personal affective tag, which indicates the emotional category with the degree of its distinctiveness, within the image file containing the scene image, as part of the image metadata (step 246). Alternatively, the personal affective tag, which indicates the emotional category with the degree of distinctiveness, can be stored in a separate file in association with the user identifier and the image identifier. In addition, the information about the date that the user views a certain image (i.e. immediately upon capture) can be also recorded as a separate entry into the personal affective tag.

In another embodiment the raw facial images are stored as affective information either in a separate file on the image capture device 6 together with the image identifier and the user identifier, or in the personal affective tag as part of the image metadata, and the analysis is done at a later time and optionally using a separate system. For example, the scene image and raw facial image can be communicated using the wireless modem 18 (see FIG. 1) and the Internet Service Provider 20 to a separate desktop computer (not shown) or computer server (not shown), which can perform the analysis described earlier in relation to steps 234-238.

The recipient is identified in a manner that is similar to step 147 of FIGS. 2*a* and 2*b*. The emotional category and the degree of its distinctiveness used as the source of affective information (step 247).

The corresponding image, the personal affective tag and other image metadata are sent using the communication module 18 to Internet Service Provider 20 or some other communication network to a recipient e.g. a personal database of digital images (step 248). This personal database of images can be stored, for example, using separate desktop computer (not shown) or computer server (not shown).

In another embodiment, the corresponding image, the personal affective tag, image metadata including derived image information are sent to a physician or other health care provider for additional analysis of a particular affective reaction of the user to a specific situation or a review (step 248). The corresponding image, the personal affective tag, image metadata and derived image information can also be sent to a member of a support network, including family members or local emergency services.

Feedback information is displayed on the camera preview screen 22 or the communication screen 21 (step 250). This information is automatically generated by the appropriate software program and may contain an image of the scene, the determined emotional category with the degree of distinctiveness, or both. It may also include or solely consist of a sound signal, pre-recorded voice message or computer generated speech. In another embodiment, a feedback can be sent by a physician or a member of the support network to facilitate therapy or otherwise assist user 2 in this regard, an interactive communication exchange can be initiated.

If the criterion specified in step 240 was not met, e.g., the obtained degree of distinctiveness is below the threshold value, the facial image of the user and the scene image are deleted.

If the obtained degree of distinctiveness is below the threshold value and if user 2 is still viewing the same scene or captured image of the scene, such as for example on preview screen 22, image capture device 6 can optionally capture the next facial image and repeat steps 232 through 240 to determine if user 2 has changed her facial expression as user 2 views the scene or the captured image of the scene.

If the threshold value is set to 0, all scene images and corresponding affective information (emotional category with the degree of distinctiveness or in another embodiment, raw facial image) recorded by the image capture device 6 will be permanently stored as affective information either in a separate file on the image capture device 6 together with the image identifier and the user identifier, or in the personal affective tag as part of the image metadata.

If user 2 keeps the power turned on, the process of capturing the next image of the scene (steps 220-223) and simultaneously determining and storing a personal affective tag for the captured image (steps 230-246) are repeated (step 226).

Image capture device 6 continues recording images of the scene 4 using capture module 8 and facial images of the user 2 using user video camera 10, as long as user 2 keeps the image capture device 6 powered on. If the power is turned off, the image capture device 6 stops recording the images of the scene and the facial images and also ends the process of affective tagging (step 228).

Figure 4A:
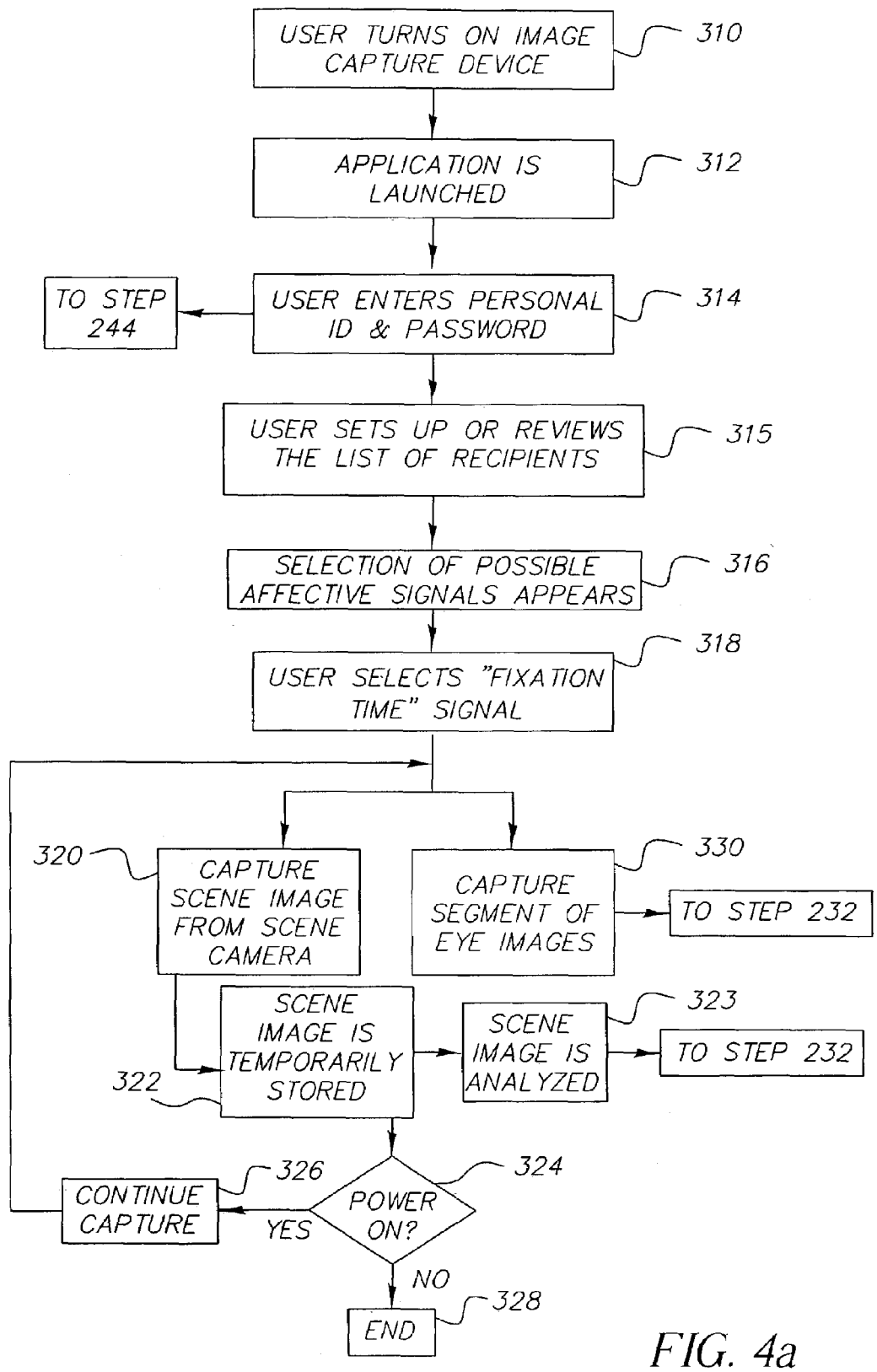
FIGS. 4a-4b comprise a flow diagram showing a method where affective information is provided based on analysis of eye gaze fixation time.
Figure 4B:
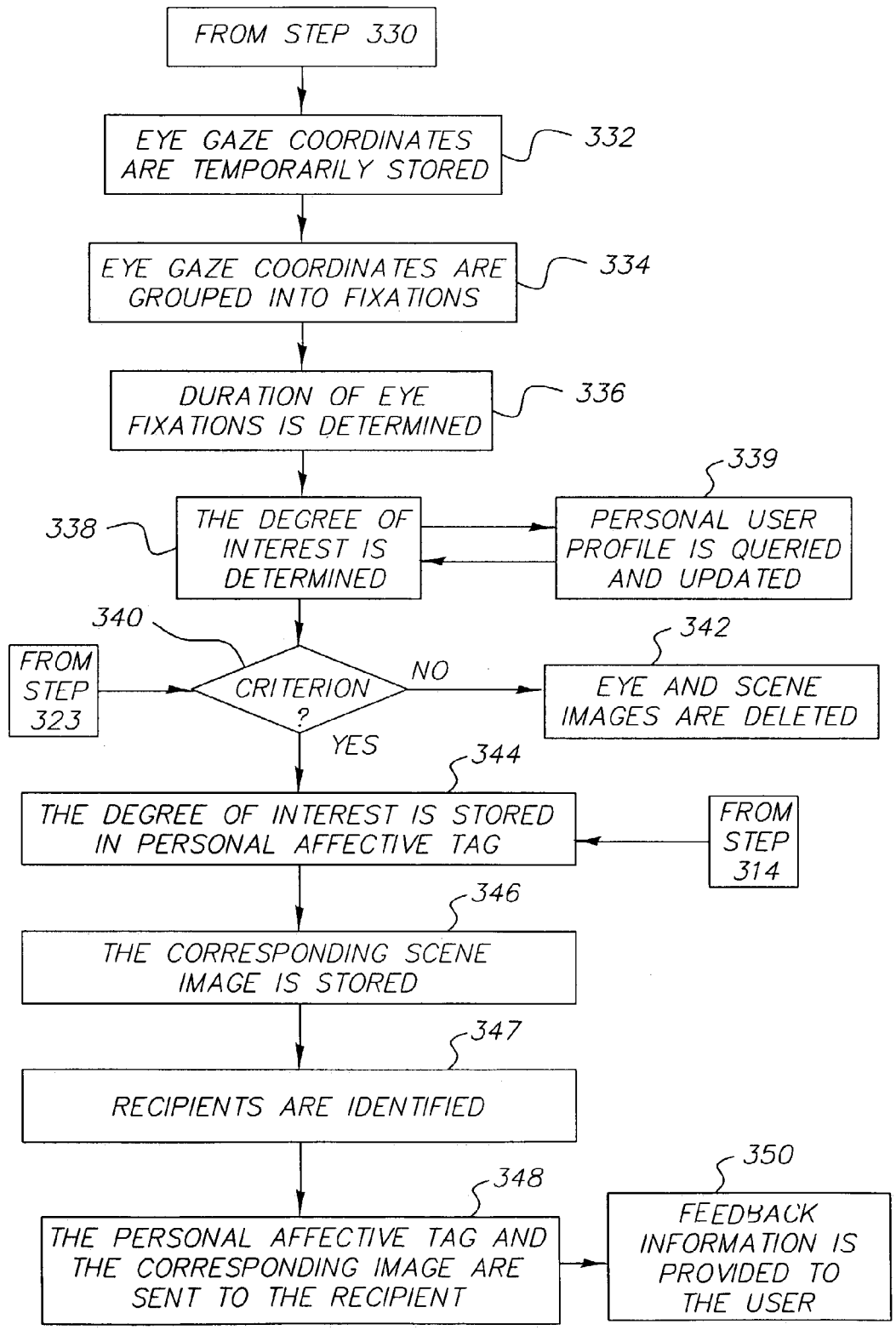

In previously discussed embodiments affective information was extracted from facial characteristics of user 2. FIGS. 4*a* and 4*b* show a flow diagram illustrating another embodiment of the present invention where affective information is provided in terms of the degree of interest based on a physiological factor, namely eye gaze fixation time. With this embodiment, a degree of interest is determined based on eye gaze fixation time which is the time that eyes of user 2 are fixated at a particular location of the scene, before fixating at a different location.

The data described in a paper entitled "Looking at pictures: Affective, facial, visceral, and behavioral reactions", published in Psychophysiology, 30, pp. 261-273, 1993, by Lang et al., indicates that on average, viewing time linearly correlates with the degree of the interest or attention an image elicit in an observer. Thus, such a relationship allows interpreting the fixation time as the user's degree of interest toward an area of a scene. The quoted publication by Lang et al. compares a viewing time with the degree of the interest for third party images of scenes only. In the present invention, fixation time information is assessed directly for scenes as well as first party images of the scenes and stored as a personal affective tag as part of the image metadata or in a separate file in association with the user identifier and the image identifier.

In the embodiment of FIGS. 4*a* and 4*b*, method steps 310-328 generally correspond to method steps 110-128 in FIGS. 2*a* and 2*b* with only one difference: in step 318, the user selects the "fixation time" signal. Alternatively, the image capture device 6 can be preprogrammed to capture the "fixation time" information.

In this embodiment user video camera 10 in image capture device 6 captures a sample of eye images of an eye of user 2 during a time window, such as a time window of 30 seconds, when user 2 views the scene during one of image composition, capture and/or immediate post capture review (step 330). In some embodiments, the time window can be modified by user 2.

Concurrently, scene image is analyzed in step 323, as is described in greater detail above with reference to step 123 described of FIGS. 2*a* and 2*b*.

Coordinates of the eye gaze direction of user 2 are stored with a sampling rate, such as a sampling rate of 60 Hz (step 332). In some embodiments, the sampling rate can be modified by user 2. The sampling rate can also be modified based upon other factors such as the rate of charge from the eye gaze as the time rate of change of scene contents or the amount of memory available for storing affective data.

The raw gaze coordinates are grouped into eye fixations (step 334). An eye fixation is usually defined as period of at least 50 msec during which the gaze coordinates do not change by more than 1-degree of visual angle. For each fixation, a start time, end time and gaze coordinates are determined. Additionally, an average pupil diameter can be determined for each fixation. The duration of eye fixations are measured based on their start and end times (step 336).

Image capture device 6 determines the degree of interest for each eye fixation (step 338). The absolute degree of interest is defined as the corresponding fixation time. The relative degree of interest is defined as the fixation time divided by the average fixation time for the particular user. The average fixation time can be constantly updated and stored on digital storage device 12 as a part of a personal user profile for user 2. The personal user profile is queried and updated with respect to the average fixation time for user 2 (step 339).

Subsequent steps 340-350 correspond to steps 140-150 and 240-250 described in relation to the previous embodiments illustrated in FIGS. 2a and 2b and 3a and 3b respectively, with the difference concerning the type of affective information recorded in a personal affective tag in step 344. That is, in this embodiment the degree of interest is recorded in the affective tag.

In one embodiment, image capture device 6 stores the degree of interest in the personal affective tag as part of the image metadata together with the corresponding image (step 346). The data is stored in the image metadata that can comprise data that characterizes the personal affective information or can comprise data indicating the location of the file having the personal affective information. In addition, the information about the date the user views a certain image can be also recorded as a separate entry into the personal affective tag.

In another embodiment the scene images and the raw eye images are stored. The raw eye images can be analyzed later, either by the CPU 14 or by a processor in a separate device (not shown).

If the obtained degree of interest is below the threshold value, the galvanic skin response signal of user 2 and the scene image are deleted (step 342).

In another embodiment, if the obtained degree of interest is below the threshold value set in step 340, and user 2 is still viewing the same captured image such as, for example, on a preview screen 22 image capture device 6 can optionally capture another segment of eye images and repeat steps 332 through 340 to determine if user 2 has changed the degree of interest in the captured image.

If the threshold value is set to 0, all scene images and corresponding affective information (degree of interest or, in another embodiment, raw eye images) recorded by the image capture device 6 can be stored as affective information either in a separate file on the image capture device 6 together with the image identifier and the user identifier, or in the personal affective tag as part of the image metadata.

In alternative embodiments, user video camera 10 and central processing unit 14 can be used to obtain additional information from images of at least one of the eyes of the user. Examples of such information include but are not limited to eye all acceleration, tear formation, eye temperature, iris patterns, blood vessel patterns and blood vessel size. This information can be used to determine the identity, emotional state and/or health condition of user 2. This information can be stored as part of an affective tag.

Figure 5A:
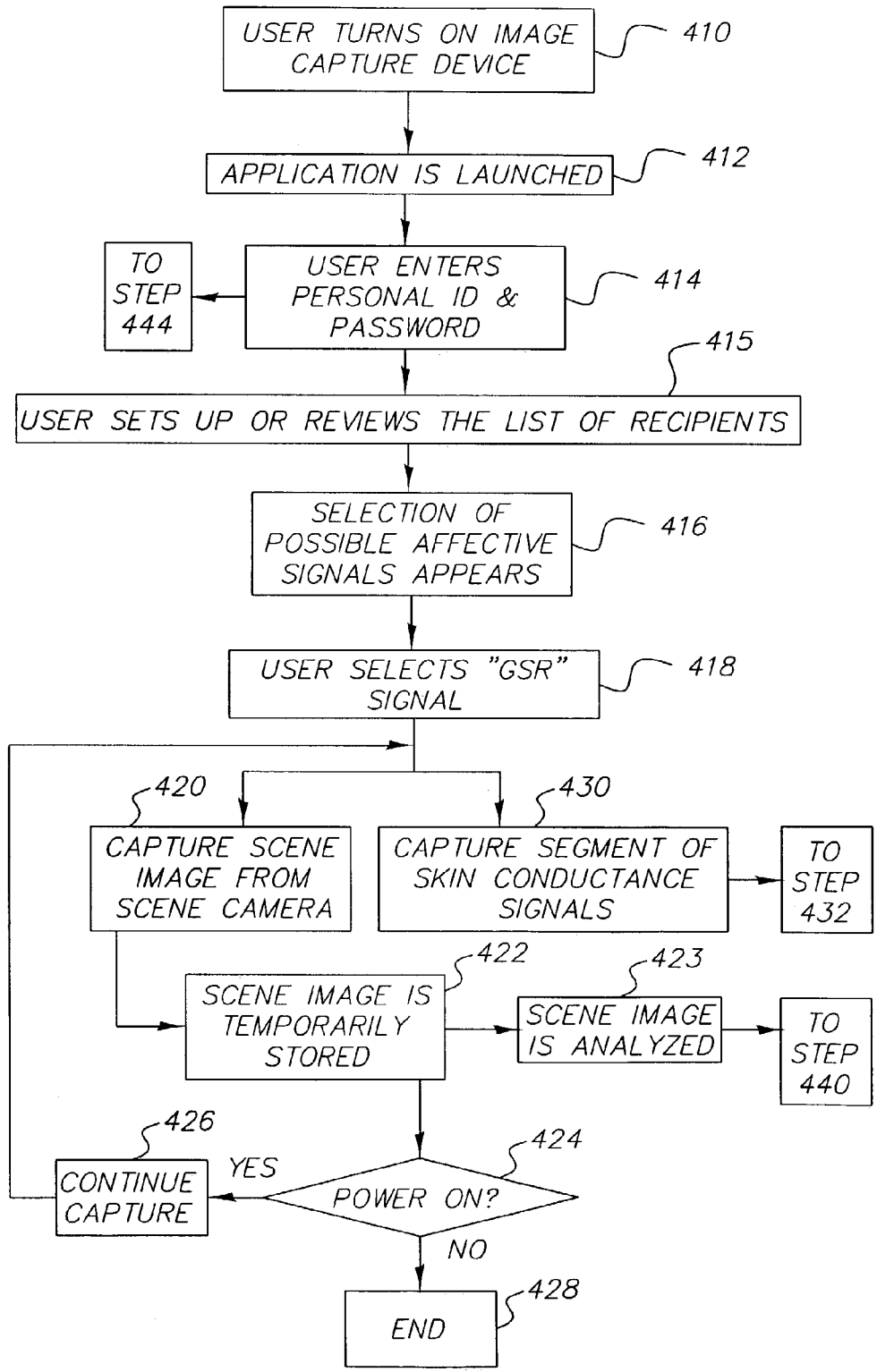
FIGS. 5a-5b comprise a flow diagram showing an embodiment of a method where affective information is provided based on analysis of skin conductance.
Figure 5B:
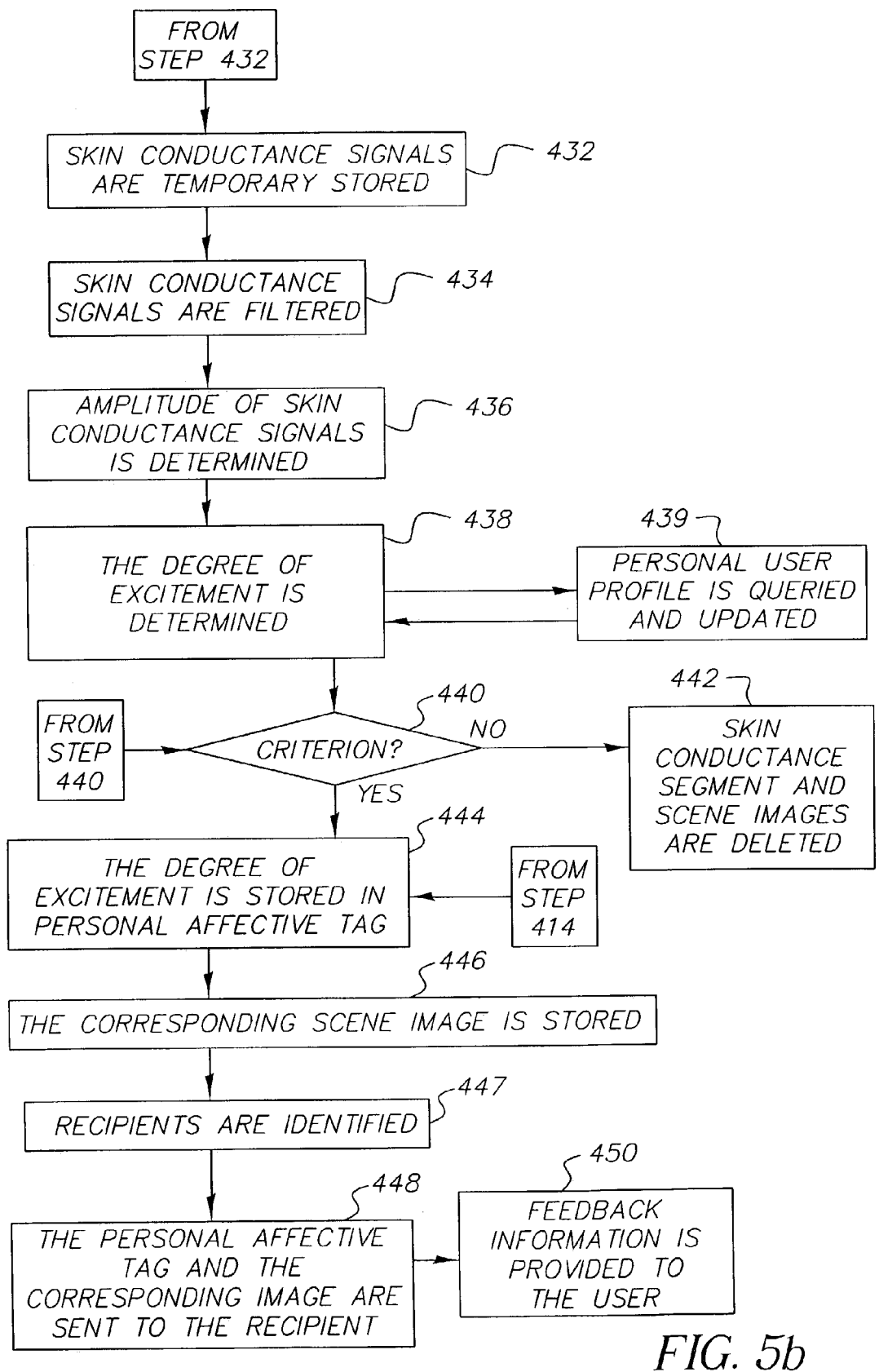

Another source of affective information originates from physiological signals generated by user 2. FIGS. 5a and 5b illustrate an embodiment of the present invention where affective information is determined from a physiological signal. In this embodiment, the physiological signal is a skin conductance signal and the affective information derived from the skin conductance signal is expressed in terms of a degree of excitement.

Skin conductance change is a measure of galvanic skin response. Skin conductance reflects a change in a magnitude of the electrical conductance of the skin that is measured as a response to a certain event—viewing the scene or images of the scene. As described in the paper "Looking at Pictures: Affective, Facial, Visceral, and Behavioral Reactions", published in *Psychophysiology*, 30, pp. 261-273, 1993, by Lang, et al. skin conductance changes depending on the arousal the image elicits in the viewer: the higher the conductance, the lower the arousal or excitement, and vice versa: the lower the conductance, the higher the arousal. The measure of the amplitude of the skin conductance response is also used to determine interest or attention.

In this embodiment, method steps 410-428 generally correspond to 110 through 128 in FIGS. 2a and 2b with only one difference: in step 418, the user can manually instruct image capture device 6 to capture galvanic skin response information as at least a part of the affective information. Alternatively, image capture device 6 can be preprogrammed to capture galvanic skin response information. Image capture device 6 measures the galvanic skin response signal during a time window, for example a time window of 5 seconds, using the physiological sensor 16 (step 430). In some embodiments, the time windows can be modified by the user. One example of a galvanic skin response sensor 16 is the SC-Flex/Pro+ and Procomp detection system by Thought Technology Ltd. W. Chazy, N.Y. USA.

The galvanic skin response skin conductance signals are stored, for example, using a sampling rate, for example a sampling rate of 60 Hz (step 432). In some embodiments, the sampling rate can be modified by user 2. The sampling rate can also be modified based upon other factors such as the rate of change of scene contents, the time rate of change of galvanic skin response, or the amount of memory available for storing affective data. The galvanic skin response skin conductance signals are filtered to reduce the noise in the data (step 434). The amplitude of the galvanic skin response signal is then determined (step 436).

Image capture device 6 determines the degree of excitement (step 438). The absolute degree of excitement for the scene is equivalent to the amplitude of the filtered galvanic skin response skin conductance signal. The relative degree of excitement is defined as the amplitude of the galvanic skin response signal divided by the average galvanized skin response signal for the particular user. The average skin conductance can be constantly updated and stored on digital storage device 12 as a part of the user's psychophysiological profile. To compute the relative degree of excitement, the average skin conductance response information is retrieved from a personal user profile. The personal user profile is updated regarding the skin conductance response information (step 439).

The obtained degree of excitement is compared to a criterion, which is constructed to reflect the significance of both affective information and image information extracted in steps 423 and 438 (step 440). Such criterion can be defined for example in the form of the logical "OR" expression. That is if the relevant information in the scene image is detected, or a threshold value for the affective information, namely the degree of excitement in this case, is exceeded, or both a detection of the relevant scene image information and surpassing the threshold for the degree of excitement took place, the criterion in the step 440 is met. It is also understood that the criterion in step 440 can be set to give a priority to either of the two sources of information.

In one embodiment the criterion may reflect only the significance of affective information, namely the degree of excitement. In this embodiment the obtained degree of excitement is compared to a threshold value established by user 2 or for user 2 (step 440). If the obtained degree of excitement is above the threshold value, then the image capture device 6 creates a personal affective tag for the corresponding image which indicates a degree of excitement for this particular captured image (step 444). In another embodiment the threshold value for the degree of excitement could also be established automatically from the personal user profile, for example, on the basis of the prior cumulative probabilities for the user's degrees of excitement distribution. Such probability could be equal to 0.5, and thus, the threshold value for the degree of excitement would correspond to the value that occurs in at least 50% of the cases. Alternatively, the personal affective tag can include a value selected from a range of excitement values, enabling the differentiation of the relative degree of excitement between various captured images.

If the criterion in step 440 is met, image capture device 6 stores the corresponding image and the personal affective tag, which indicates the degree of excitement, within the image file containing the scene image, as part of the image metadata (steps 444 and 446). Alternatively, the personal affective tag, which indicates the degree of excitement, can be stored in a separate file in association with the user identifier and the image identifier. In addition, the information about the date that the user views a certain image (i.e. immediately upon capture) also can be recorded as a separate entry into the personal affective tag.

In another embodiment the raw galvanic skin response signals are stored as affective information either in a separate file on image capture device 6 together with the image identifier and the user identifier, or in the personal affective tag as part of the image metadata, and the analysis is done at a later time and optionally using a separate system. For example, the scene image and raw galvanic skin response signals can be communicated using the wireless modem 18 (see FIG. 1) and the Internet Service Provider 20 to a separate desktop computer (not shown) or computer server (not shown), which can perform the analysis described earlier in relation to steps 434-438.

The recipient is identified in a manner that is similar to step 147 of FIGS. 2a and 2b with the emotional category and the degree of distinctiveness used as a source of affective information (step 447). In one embodiment, the recipient can be a personal database, with an e-mail or world wide web address supplied by Internet Service Provider 20. In another embodiment the recipient can be a health care provider, or a security agency. Yet in another embodiment there could be the multiple recipients from the list including a personal database, a health care provider, friends, family members, security agency, etc. The recipients can also be automatically chosen based on the analysis of affective information, image data and non-image data. In this case, such determination as part of the step 447 can consist of, for example, comparing the value for affective information, such as the degree of excitement determined in step 438 with the pre-specified thresholds corresponding to each of the recipients from the list of recipients.

In another embodiment the threshold values for the degree of preference corresponding to each of the recipients is established automatically from the personal user profile, for example, on the basis of the prior cumulative probabilities for the user's degrees of preference distribution. In one embodiment a cumulative probability of 0.9, could be chosen for a health care provider and thus, the threshold value for the degree of preference would correspond to the value that is exceeded in only 10% of the cases.

In yet another embodiment, the personal affective tag can include a value selected from a range of preference values, enabling the differentiation of the relative degree of preference between various captured images. In a different embodiment the recipients can be chosen based on solely the results of the scene image analysis or a combination of the scene information and affective information depending on the criterion construction in the step 440.

The corresponding image, the personal affective tag and other image metadata can be sent using the communication module 18 and a communication network such as that provided by Internet Service Provider 20 to transfer the image to the identified recipient, e.g. a personal database of digital images (step 448). This personal database of images can be stored, for example, using separate desktop computer (not shown) or computer server (not shown).

In another embodiment, the corresponding image, the personal affective tag, image metadata including derived image information are sent to a physician or other health care provider for additional analysis of a particular affective reaction of the user to a specific situation or a review. In can also be sent to a member of the support network, including family members or local emergency services.

Feedback information is displayed on the camera preview screen 22 or communication screen 21 (step 450). This information is automatically generated by the appropriate software program and may contain an image of the scene, the determined degree of excitement, or both. It may also include or solely consist of a sound signal, pre-recorded voice message or computer generated speech or images. In another embodiment, a feedback can be sent by a physician or a member of the support network to facilitate therapy.

If the obtained degree of excitement is below the threshold value, the galvanic skin response signal of user 2 and the scene image are deleted (step 442). In another embodiment, if the obtained degree of excitement is below the threshold value and if user 2 is still viewing the same scene or a captured image of the scene, such as for example on preview screen 22, image capture device 6 can optionally capture the next galvanic skin response segment and repeat steps 432 through 440 to determine if user 2 has changed skin conductance response as user 2 views the captured image.

If the threshold value is set to 0, all scene images and corresponding affective information (degree of excitement or in another embodiment, raw galvanic skin response signal) recorded by the image capture device 6 will be permanently stored as affective information either in a separate file on the image capture device 6 together with the image identifier and the user identifier, or in the personal affective tag as part of the image metadata.

It is understood that each user 2 might have different physiological and facial responses to an image. Some users might exhibit strong physiological responses while exhibiting only modest facial responses. Other users might exhibit modest physiological responses while exhibiting strong facial responses. Still other users might exhibit modest physiological and facial responses. Accordingly, by combining different types of affective information, a more robust representation of the emotional response of user 2 to the scene can be obtained. The following embodiments show methods for interpreting affective information using physiological and facial response information in combination to help facilitate interpretation of affective information.

Figure 6A:
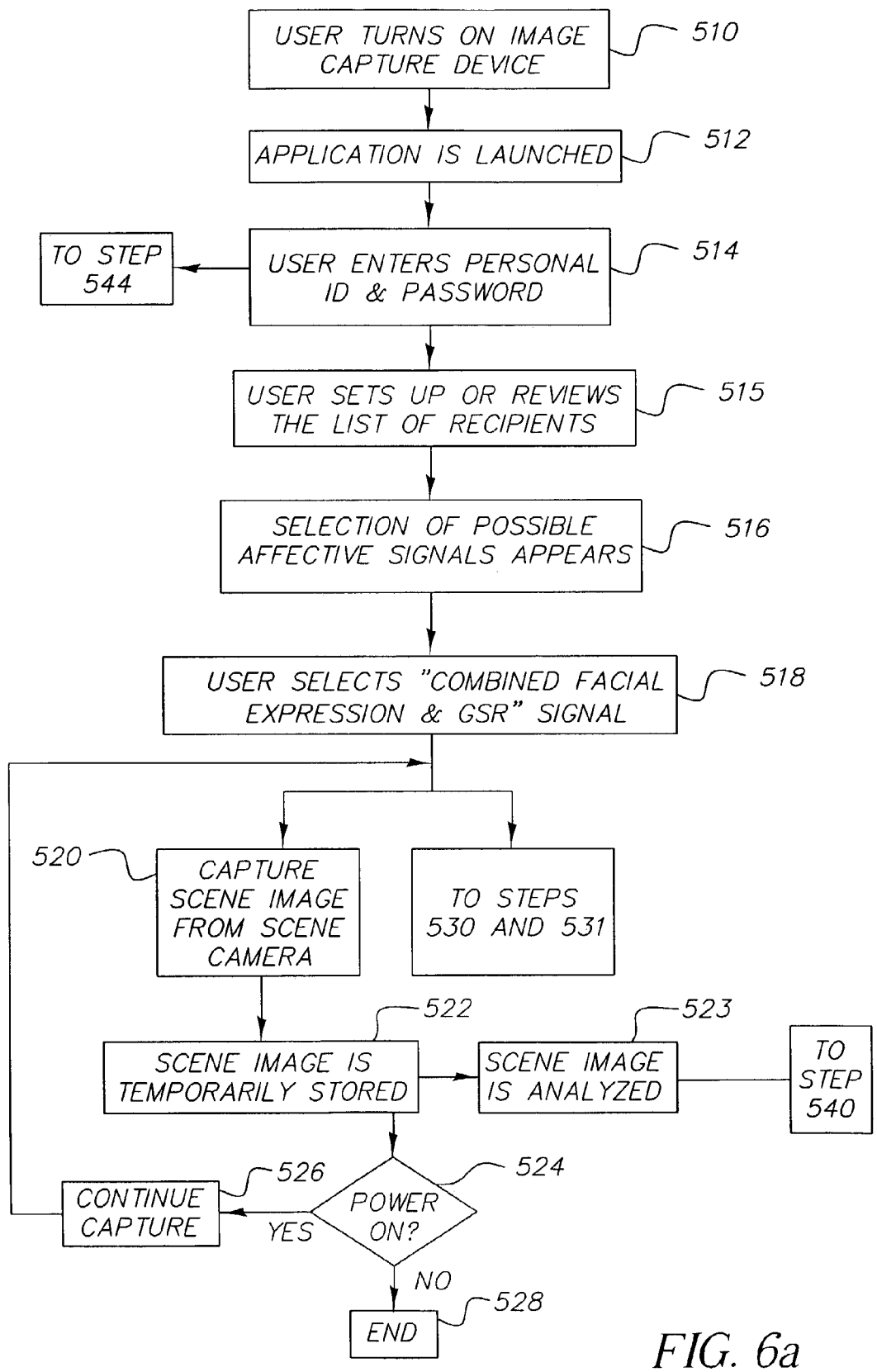
FIGS. 6a-6b comprise a flow diagram showing an embodiment of a method where affective information is provided based on combined analysis of facial and physiological characteristics.
Figure 6B:
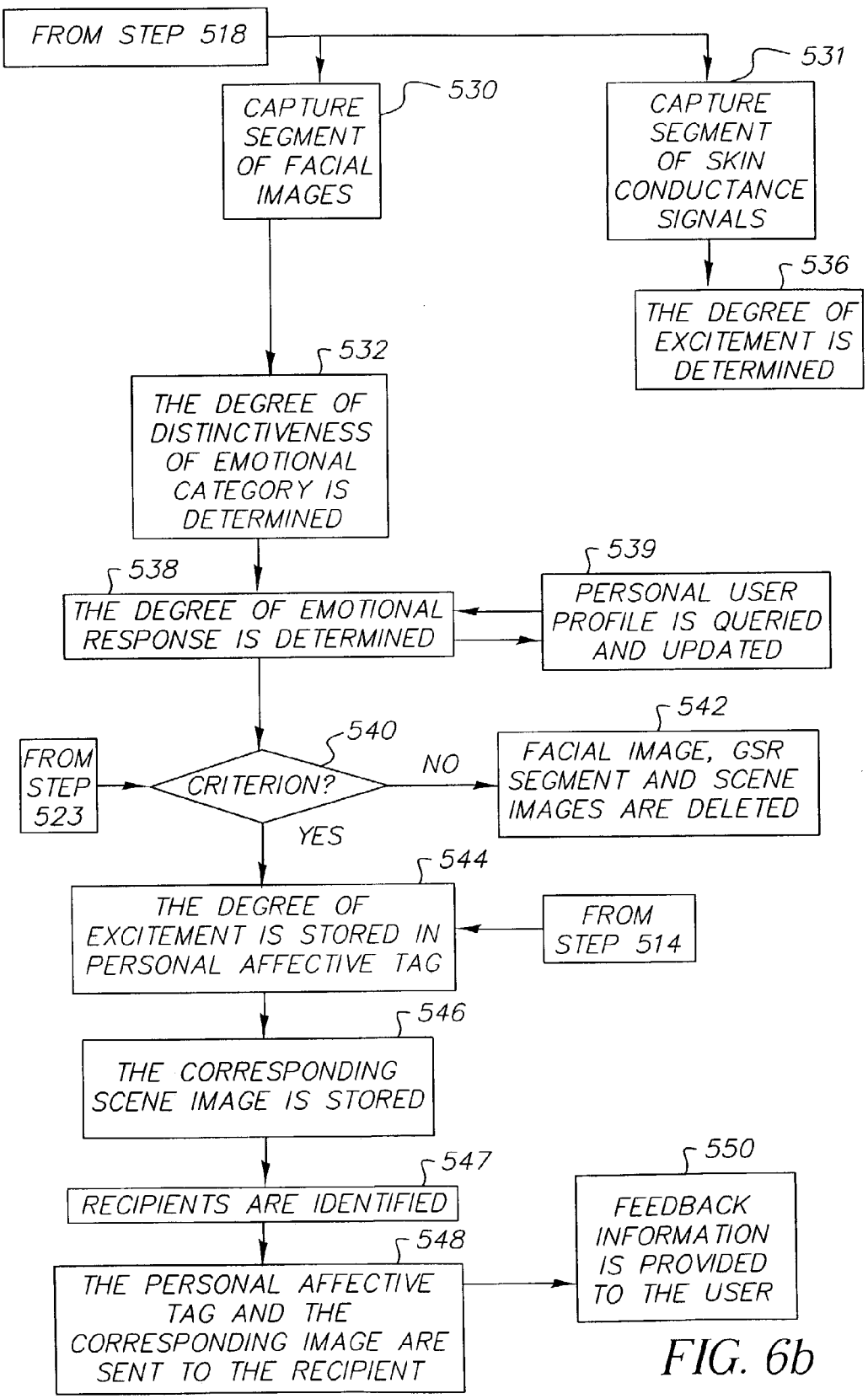

Referring to FIGS. 6a and 6b, there is shown a flow diagram illustrating an embodiment of the present invention for providing affective information based on the combination of the affective signals described in relation to FIGS. 3a, 3b, 5a and 5b and 5, namely, the degree of distinctiveness of the determined emotional category and the degree of excitement, which are further combined to obtain an integral measure of emotional response.

In this embodiment, method steps 510-528 correspond to method steps 110 through 128 in FIGS. 2a and 2b with only one difference: in step 518, the user selects "combined facial expression and galvanic skin response" (further in the text referred to as "combined") signals or alternatively, the image capture device 6 is preprogrammed to use the "combined" signals.

Consequently, the image capture device 6 captures a facial image of user 2 and skin conductance information (steps 530 and 531 respectively).

Image capture device 6 determines the degree of distinctiveness of emotional category ($DD_{EC}$) based on facial expression as was described earlier in relation to steps 232 through 238 in FIG. 3 (step 532). Image capture device 6 determines the degree of excitement (DE) based on skin conductance the same way as in steps 432 through 438 in FIG. 5 (step 536).

Image capture device 6 determines the magnitude of emotional response (step 538). This can be done in a variety of ways. For example the magnitude of the emotional response can be based on a sum of the two measures:

Emotional Response=$DD_{EC}$+DE

Information about particular emotion the user experienced in documented by referring to the emotional category EC.

In another embodiment, the magnitude of emotional response is determined as a square root of the sum of the squared measures, Emotional Response=$\sqrt{DD_{EC}^2+DE^2}$ In yet another embodiment, the magnitude of emotional response can be computed as a weighted sum of the two measures, Emotional Response=$w_{DD} DD_{EC}+w_{DE} DE$ where the weights $w_{DD}$ and $w_{DE}$ are determined based on the standard deviation within each of the normalized (divided by the maximum value) signals previously obtained for the particular user. In this case, the higher the standard deviation within the signal, the higher the weight of the contribution for the signal into the measure of emotional response. Consequently, the lower the standard deviation of a given signal, the lower the weight of the contribution for the corresponding signal into the measure of emotional response. The reason for this dependency stems from the assumption that a standard deviation of a particular measure for a particular user reflects an individual degree of differentiation between different scenes. This implies that the signal with the highest standard deviation has more differentiation power, and therefore is more emotional response for a particular user.

For example, if different scenes evoke a large variations of facial expression and a low variation of skin conductance responses for a user A, than the weight given to the measure of the degree of distinctiveness of emotional category ($DD_{EC}$) based on facial expression $w_{DD}$ would be higher than the weight given to the measure of the degree of excitement (DE) based on skin conductance $w_{DE}$. On the other hand, if different scenes evoke smaller variations of facial expression and a large variation of skin conductance responses for a user B, than the relationships between the weights is reversed. Data about the maximum values and the standard deviation of the corresponding signals can be obtained from the personal user profile (step 539). The personal user profile is then updated regarding this information.

The obtained magnitude of emotional response is compared to the criterion, which reflects the significance of both affective information and image information extracted in steps 523 and 538, similarly to other embodiments described previously (step 540).

If the criterion is met, image capture device 6 stores the corresponding image and the personal affective tag, which indicates the magnitude of emotional response, within the image file containing the scene image, as part of the image metadata (steps 544 and 546). Alternatively, the personal affective tag, which indicates the magnitude of emotional response, can be stored in a separate file in association with the user identifier and the image identifier. In addition, the information about the date that the user views a certain image (i.e. immediately upon capture) can be also recorded as a separate entry into the personal affective tag.

In another embodiment the raw galvanic skin response signals and the facial image are stored as affective information either in a separate file on the image capture device 6 together with the image identifier and the user identifier, or in the personal affective tag as part of the image metadata, with the analysis being done at a later time and optionally using a separate system. For example, the scene image, the facial image and raw galvanic skin response signals can be communicated using the wireless modem 18 (see FIG. 1) and the Internet Service Provider 20 to a separate desktop computer (not shown) or computer server (not shown), which can perform the analysis described earlier in relation to steps 532-538.

The recipient is identified (step 547) in a manner similar to step 147 of FIGS. 2a and 2b above. In one embodiment, the recipient can be a personal database, with an e-mail or world wide web address supplied by Internet Service Provider 20. In another embodiment the recipient can be a health care provider, or a security agency. In another embodiment there could be the multiple recipients from the list including a personal database, a health care provider, friends, family members, security agency, etc. The recipients can also be automatically chosen based on the analysis of affective information, image data and non-image data. In this case, such determination as part of the step 547 can consist of, for example, comparing the value for affective information, such as the magnitude of emotional response determined in step 538 with the pre-specified thresholds corresponding to each of the recipients from the list of recipients.

In another embodiment the threshold values for the magnitude of emotional response corresponding to each of the recipients are established automatically from the personal user profile, for example, on the basis of the prior cumulative probabilities for the user's emotional response distribution. In one embodiment a cumulative probability of 0.9, could be chosen for a health care provider and thus, the threshold value for the magnitude of emotional response would correspond to the value that is exceeded in only 10% of the cases.

In yet another embodiment, the personal affective tag can include a value selected from a range of response values, enabling the differentiation of the relative magnitude of emotional response between various captured images. In a different embodiment the recipients can be chosen based on solely the results of the scene image analysis or a combination of the scene information and affective information depending on the criterion construction in the step 540.

The corresponding image, the personal affective tag and other image metadata are sent using the communication module 18 on Internet Service Provider 20 to the identified recipient, e.g. a personal database of digital images (step 548). This personal database of images can be stored, for example, using separate desktop computer (not shown) or computer server (not shown).

In another embodiment, the corresponding image, the personal affective tag, image metadata and derived image information are sent to a physician or other health care provider for additional analysis of a particular affective reaction of the user to a specific situation or a review. In can also be sent to a member of the support network, including family members.

Feedback information is displayed on a camera preview screen 22 or a communication screen 21 (step 550). This information is automatically generated by the appropriate software program and may contain an image of the scene, the determined magnitude of emotional response, or both. It may also include or solely consist of a sound signal, pre-recorded voice message or computer generated speech or images.

In another embodiment, a feedback can be sent by a physician or a member of the support network to facilitate therapy.

If the obtained magnitude of emotional response is below the threshold value the facial image, the galvanic skin response signal of the user and the scene image are deleted (step 542).

In another embodiment, if the obtained response magnitude for the determined emotion is below the threshold value and if user 2 is still viewing the same scene or captured image of the scene, such as for example on preview screen 22, image capture device 6 can optionally capture the next facial image and galvanic skin response segment and repeat steps 532 through 540 to determine if user 2 has changed her facial expression and skin conductance response as user 2 views the scene or captured image of the scene.

If the threshold value is set to 0, all scene images and corresponding affective information (the magnitude of emotional response or in another embodiment, raw facial image and galvanic skin response signal) recorded by the image capture device 6 will be permanently stored as affective information either in a separate file on the image capture device 6 together with the image identifier and the user identifier, or in the personal affective tag as part of the image metadata.

In another embodiment, different combinations of facial expressions, eye characteristics and physiological reactions can be used to create the personal affective tag to classify scenes in accordance with a broad range of emotional categories, such as 'joy', 'fear', 'anger', etc. An example of such classification is shown in Table 1.

TABLE 1

Emotion classification based on combinations of facial expressions, eye characteristics and physiological reactions

| Signals Emotion | Facial expressions | Eye characteristics | Physiological reactions |
| --- | --- | --- | --- |
| Joy | smile, crinkled skin around eyes corners | opened eyelids, dilated pupils, direct gaze | accelerated heart rate, large GSR |
| Fear | pale skin, trembling lips, chattering teeth | widely opened eyelids, fast eye-blink rate, fixed gaze, dilated pupils | accelerated heart rate accelerated breathing rate, tightened muscle tension, sweaty palms |

TABLE 1-continued

Emotion classification based on combinations of facial expressions, eye characteristics and physiological reactions

| Signals Emotion | Facial expressions | Eye characteristics | Physiological reactions |
| --- | --- | --- | --- |
| Anger | lowered brows, flared nostrils, horizontal wrinkles over nose bridge, tense-mouth | narrowed eyelids, fixed gaze, | deep and rapid breathing, increased blood pressure |
| Surprise | raised eyebrows, opened mouth, wrinkled brow and forehead | opened eyelids, fixed gaze | large GSR |
| Disgust | wrinkled nose, raised nostrils, retracted upper lip, visible tongue, lowered brows | narrowed eyelids, averted gaze | decreased breathing rate |
| Sadness | lowered lips, cheeks, and jaw | narrowed eyelids, tearing eyes, down gaze | flaccid muscles, decreased breathing rate |

Different combinations of the signals described in FIGS. 2a, 2b, 3a, 3b, 4a, 4b, 5a and 5b, or other affective signals (such as derived from voice, EEG, brain scan, eye movements, eye images and others) can be used to create the personal affective tag to classify scenes in accordance with broader range of emotional categories.

Images can be further classified using a range of values for these categories, such as strongly happy, somewhat happy, neutral and somewhat sad, and strongly sad, etc.

The determined affective information in terms of the emotional category is then stored as personal affective tag, which includes the user identifier as part of the image metadata. It can also be stored in a separate file on a computer together with the image identifier and the user identifier.

A computer program for creating and using personal affective tags in an image capture device can be recorded on one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for practicing a method according to the present invention.

The personal affective tag can also include information designating a relative magnitude of emotional response. As described earlier, the relative magnitude of emotional response can be determined on the basis of affective information only. Alternatively, affective and non-affective information can be used in combination to determine the relative magnitude of emotional response. Examples of image metadata are described above and include date and time information, location information such as would be available from a Global Positioning System or a similar type of electronic locator. Image analysis of the image itself can also be used as a source of non-affective information that can influence the relative degree of importance. As it was described earlier, the presence of particular subject matter in a scene can be readily identified by existing image processing and image understanding algorithms, such as for example, disclosed in commonly assigned U.S. Pat. No.

6,282,317 entitled "Method for Automatic Determination of Main Subjects in Photographic Images" filed by Luo on Dec. 31, 1998, which describes a method for automatic determination of main subjects in photographic images. The presence of people in a scene or particular people, established using facial recognition algorithms such as described in a previously mentioned article by Liu et al. may be used to increase the relative magnitude of emotional response. It can also be used to selectively process the image in order to enhance its quality, emphasize a main subject as described by European Pat. No. EP 1211637 filed by Luo et al. on share this image with the people identified or to transmit the image to an agency because of security concerns.

Figure 7A:
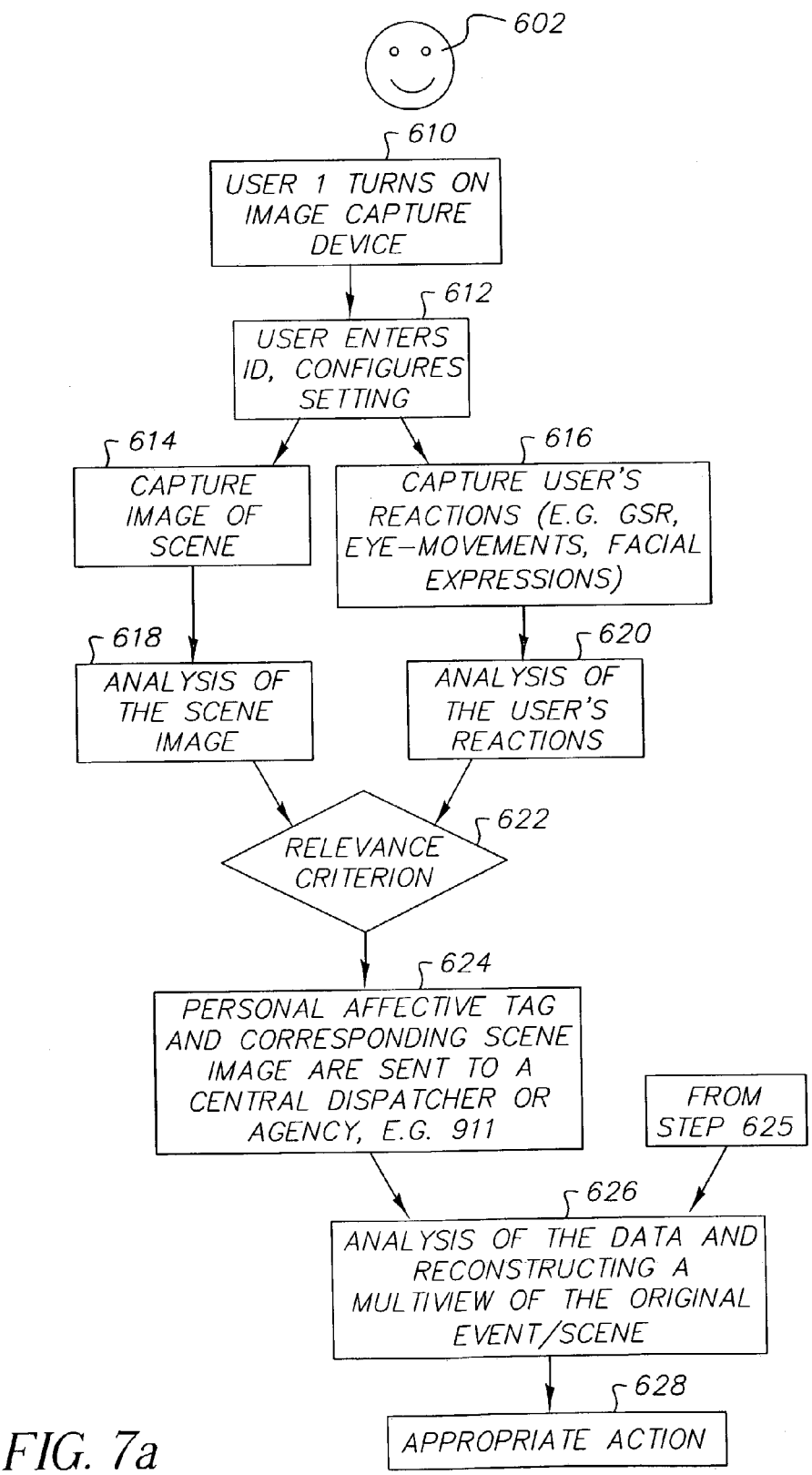
FIGS. 7a-7b comprise a flow diagram showing a method for providing a multiple source of image data and affective information with triggered transfer via a distributed capture network.
Figure 7B:
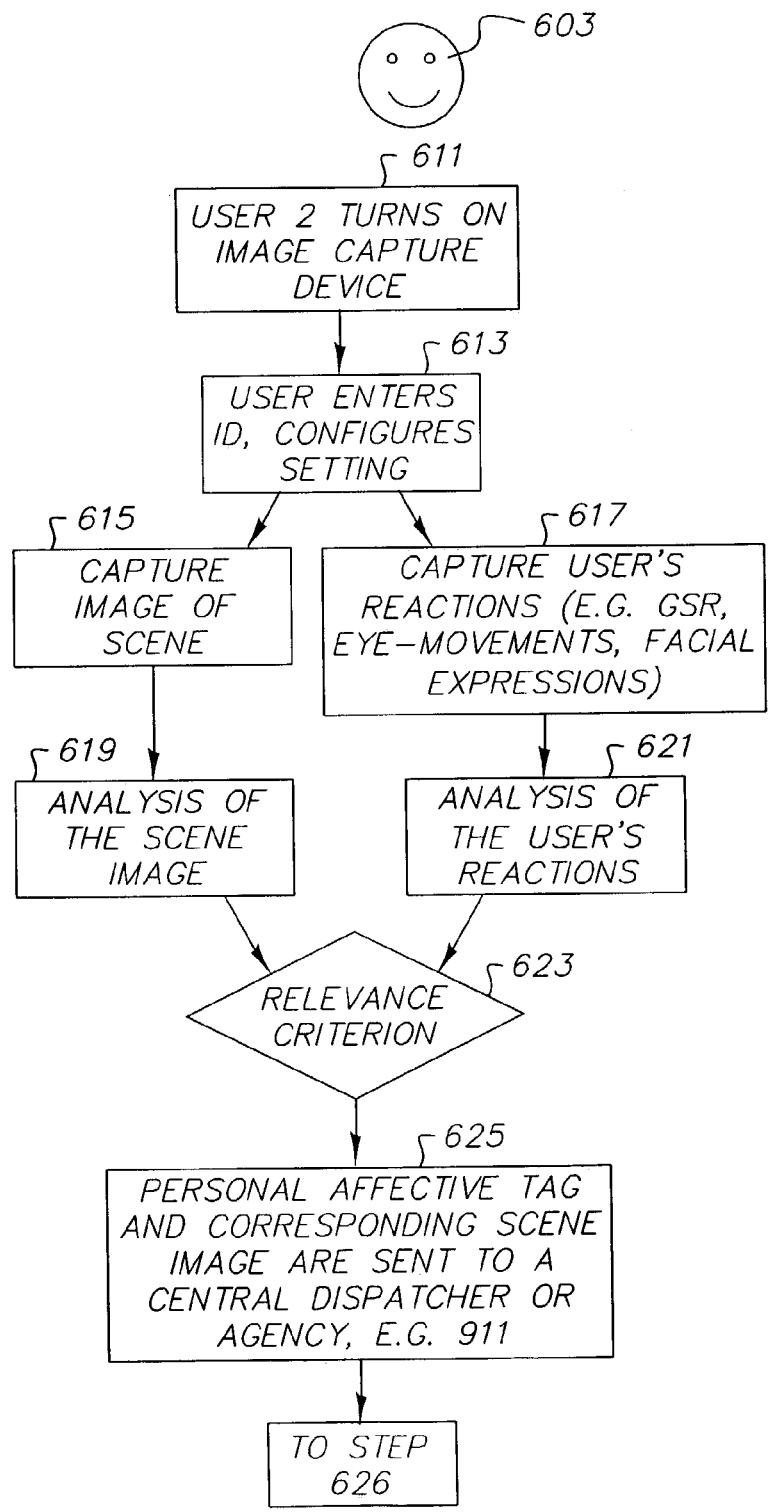

FIG. 7 illustrates an embodiment of the invention, which utilizes a number of image capture devices 6 for personal security and health monitoring, the operation of which was described in FIGS. 1-6 and uses the information obtained from each device to reconstruct details of the events and people's reactions by integrating scene images affective information from multiple users. Thus, in steps 610 and 611 the user 602 and the user 603 turn on their image capture device 6.

Users 602 and 603 enter their identification data, configure the signal setting and a recipient list as it was described earlier in relation to steps 112-118 of FIGS. 2*a* and 2*b* (steps 612 and 613). As the identification data the user ID and a password can be used. In an alternative embodiment, the user video camera 10 is used in conjunction with face recognition software to automatically determine the identity of the user, and to provide an appropriate user identifier, such as the user's name, personal identification code or fingerprints data. In another alternative embodiment, the image capture device 6 is pre-programmed with user identification data. Consequently, entering the user identification data is not required.

The image capture device 6 in possession of the first user 602 acquires an image of the event and the first user's reactions (steps 614 and 616).

In parallel, a similar image capture device 6 in possession of the second user 603 captures a different image of the event and the second user's reactions in steps 615 and 617.

The analysis of the images of the event is automatically performed in step 618 for the first user and step 619 for the second user. The analysis of the scene is done using similar to the process earlier described in relation to step 123 with the goal to identify a particular subject matter, or to classify the scene image, such as for example an accident, a crime scene, an explosion, etc. The images can be further analyzed and used to determine the state of security or to identify people involved. The images of the scene and any affective information can also be transmitted without analysis directly sent to the central location, where such analysis is performed.

Reactions of users 602 and 603, such as physiological responses (e.g. galvanic skin response), eye movement data (e.g. fixation duration), or facial expressions or their combinations are analyzed following processes similar to those described in FIGS. 2-6 steps 132-139, 232-239, 432-439 or 532-539 (steps 620 and 621). In one embodiment, the result of this process is the determination of the magnitude of emotional response based on the combination of the degree of distinctiveness of emotional category obtained from the facial image of the user and the degree of excitement determined from the galvanic skin response signal. In an alternative embodiment, affective information in the form of raw signals without any analysis is sent to the central location, where the analysis is performed.

In steps 622 and 623 for the first and second user respectively, the results of the scene analysis and the user's reaction analysis are compared to the criterion. This criterion can reflect the relevance of the image data, the magnitude of the emotional response in relation to the pre-specified threshold, or a combination of these two types of data, similar to the previously described steps 140, 240, 340, 440 or 540 in relation to FIGS. 2, 3, 4, 5 and 6, respectively.

If the criterion is fulfilled, the personal affective tag, the corresponding scene image and non-image data, such as, for example, the date and GPS signals, are sent to the appropriate recipient, e.g., an emergency center. This is done in step 624 for the first user and in step 625 for the second user. The information can also be sent to the personal users' databases.

The information received from the image capture devices 6 in possession of different users is analyzed and compared (step 626). One way to compare such information is to sort it on the basis of the GPS signal. If the GPS signals from the two devices show that two users were at the same location, image data, affective information and other non-image data are combined to reconstruct a "multiple view" of the original event. This information can also be bundled together and used at a later time for the investigation related to the event.

An appropriate reaction is taken (step 628). An example of such a reaction could be a dispatch of the police or an ambulance to the scene. Another example of the action is a feedback provided to the user in the form of a visual or voice message using preview screen 22. In the case of the catastrophic event this feedback may contain information to guide user 2 to a place of safety.

In the embodiments described above, the image and image capture system have been described as being digital images and digital image capture systems. Consistent with the principles of the invention, images of the scene can be captured in an analog electronic form or on an optical medium such as a photographic film or plate. Where the image is captured in one of these forms, data representing affective information can be recorded in association with the image by recording affective information separately from the image with some identification code indicating the image with which the information is to be associated. Alternatively, affective information can be encoded and recorded in association with the analog electronic image. Where a photographic film is used, the affective information can be recorded optically or magnetically on the film. The affective information can also be recorded on an electronic memory associated with the film.

In accordance with the present invention, affective information is described as being collected at capture, at the time of capture or during capture. As used herein, these terms can encompass any time period wherein an image is being composed or captured. Such time periods can also include periods immediately after the moment of capture wherein a captured image or an image that represents a captured image is being reviewed in a quick review mode or preview mode such as are described in commonly assigned U.S. Pat. No. 6,441,854, entitled "Electronic Camera With Quick Review of Last Captured Image" filed by Fellagara et al. on Feb. 20, 1997 and commonly assigned U.S. patent application Ser. No. 09/012,144, entitled "Electronic Camera with Quick View and Quick Erase Features" filed on Jan. 22, 1998 by Napoli et al.

The invention has been described in detail with particular reference to certain preferred embodiments thereof, but it will be understood that variations and modifications can be effected within the spirit and scope of the invention.

PARTS LIST 2 user
4 scene
6 image capture device
8 capture module
10 user video camera
12 digital storage device
13 manual controls
14 CPU (central processing unit)
15 set of sensors
16 galvanic skin response sensors
17 vascular sensor
18 communication module
19 vibration sensor
20 Internet service provider
21 communication display
22 preview screen
23 portable communication module
24 viewfinder
26 bridge
28 glasses frame
29 side piece
110 activate image capture device step
112 launch application step
114 enter user identification data step
115 determine list of recipient step
116 determine emotional reaction step
118 select desirable signal step
120 capture scene image step
122 store scene image step
123 analyze scene image step
124 detect power on step
126 continue capture step
128 deactivate power step
130 capture facial image step
132 store facial image step
134 analyze facial image step
136 determine smile size step
138 determine degree of preference step
139 update personal user profile step
140 compare to threshold step
142 delete image step
144 create personal affective tag step
146 store image and affective tag step
147 identify recipient step
148 send image and affective tag step
150 provide feedback step
210 activate image capture device step
212 launch application step
214 enter user identification step
215 determine list of recipient step
216 determine emotional reaction step
218 select desirable signal step
220 capture scene image step
222 store scene image step
223 analyze scene image step
224 detect power on step
226 continue capture step
228 deactivate power step
230 capture facial image step
232 store facial image step
234 analyze facial expression step
236 determine emotional category step
238 determine degree of distinctiveness step
239 update personal user profile step
240 compare degree of distinctiveness to threshold
242 delete image step
244 create personal affective tag step
246 store image step
247 identify recipients step
248 send image and affective information
250 provide feedback step
310 activate image capture device step
312 launch application step
314 enter user identification step
315 determine list of recipient step
316 determine emotional reaction step
318 select desirable signal step
320 capture scene image step
322 store scene image step
323 analyze scene image step
324 detect power on step
326 continue capture step
328 deactivate power step
330 capture sample of eye gaze image step
332 store eye gaze coordinates step
334 determine fixation step
336 measure duration of fixation step
338 determine degree of interest step
339 update personal user profile step
340 compare to threshold step
342 delete image step
344 create personal affective tag step
346 store image and affective tag step
347 identify recipients step
348 send image and affective tag step
350 provide feedback step
410 activate image capture device step
412 launch application step
414 enter user identification step
415 determine list of recipient step
416 determine emotional reaction step
420 capture scene image step
422 store scene image step
423 analyze scene image step
424 detect power on step
426 continue capture step
428 deactivate power step
430 capture segment of galvanic skin response step
432 store galvanic skin response step
434 filter galvanic skin response step
436 determine amplitude of galvanic skin response step
438 determine degree of excitement step
439 update personal user profile step
440 compare to threshold step
442 delete image step
444 create personal affective tag step
446 store image and affective tag step
447 identify recipient step
448 send image and affective tag step
450 provide feedback step
510 activate image capture device step
512 launch application step
514 enter user identification step
515 determine list of recipient step
516 determine emotional reaction step
518 select desirable signal step
520 capture scene image step
522 store scene image step
523 analyze scene image step
524 detect power on step
526 continue capture step
528 deactivate power step 530 capture facial images step
532 determine degree of distinctiveness step
534 capture segment of galvanic skin response step
536 determine degree of excitement step
538 determine degree of emotional response step
539 update personal user profile step
540 compare to threshold value step
542 delete image step
544 create personal affective tag step
546 store image and affective tag step
547 identify recipient step
548 send image and affective tag step
550 provide feedback step
602 user
603 user
610 activate image capture device step
611 activate image capture device step
612 enter personal information step
613 enter personal information step
614 capture image of scene step
615 capture image of scene step
616 capture user reactions step
617 capture user reaction step
618 analysis of scene image step
619 analysis of scene image step
620 analysis of user reaction step
621 analysis of user reaction step
622 compare to criterion step
623 compare to criterion step
624 analysis and reconstruction of multi-view scene step
625 analysis and reconstruction of multi-view scene step
626 data analysis step
628 action step

What is claimed is:

1. An image capture method comprising the steps of:
   capturing an image of scene confronting a person;
   collecting affective information from the person at capture said collecting being separate from the capturing of the image of the scene;
   automatically identifying a receiver for the scene image and affective information based upon the affective information; and
   automatically transmitting the scene image and affective information to the selected image receiver.

2. The method of claim 1, wherein the image receiver is selected on the basis of an intensity of the emotional reaction and a class of the emotion, said intensity and class being determined based upon the collected affective information.

3. The method of claim 1, further comprising the steps of collecting scene information at capture and analyzing the scene information wherein the image receiver is selected based at least in part on the analysis of the scene information.

4. The method of claim 1, further comprising the steps of obtaining non-affective information at capture wherein the image receiver is selected based at least in part upon analysis of the non-affective information.

5. The method of claim 1, further comprising the step of receiving a reaction from the image receiver.

6. The method of claim 5, wherein the reaction is calculated to elicit a therapeutic response.

7. The method of claim 1, wherein the affective information incorporates data that is based upon physiological characteristics.

8. The method of claim 1, wherein the affective information incorporates data that is based upon analysis of facial characteristics.

9. The method of claim 1, wherein the affective information is determined based upon a combination of physiological characteristics and facial characteristics.

10. The method of claim 1, wherein the affective information is associated with the scene image.

11. An image capture method comprising the steps of:
    capturing an image of a scene observed by a person;
    collecting affective information from the person at the time of the capture of the image said collecting being performed apart from the step of capturing the image of the scene;
    automatically analyzing the captured image and the collected affective information to determine whether a transmission criterion is met; and
    transmitting the scene image and affective information to an image receiver when the transmission criterion is met, said image receiver being automatically identified from among a plurality of potential image receivers based upon the affective information.

12. The method of claim 11, wherein the transmission criterion includes a measure of an intensity of an emotional response to the scene, said intensity of the emotional response being determined based upon the collected affective information.

13. The method of claim 11, where the transmission criterion includes a scene subject identification.

14. The method of claim 11, wherein the affective information is associated with the scene image.

15. An imaging system comprising:
    an image capture system adapted to capture an image of a scene that is observed by a user;
    a memory which stores the captured image;
    a set of sensors not including the image capture system used to capture the scene image said set of sensor being adapted to collect affective signals from the user at capture;
    a processor adapted to determine affective information based upon the affective signals and the associate affective information with the captured image; and
    a transmitter for sending affective information to a selected receiver, wherein said processor is further adapted to automatically identify the selected image receiver based upon the associated affective information.

16. The imaging system of claim 15, wherein the processor is further adapted to select the receiver based upon the affective information.

17. The imaging system of claim 15, wherein the processor is further adapted to analyze the image and the affective information and to select the receiver based upon the analysis of the image and the analysis of the affective information.

18. The imaging system of claim 15, wherein the set of sensors comprises a user camera capturing images of a user's facial characteristics and the processor is further adapted to determine affective information based at least in part on the facial characteristics.

19. The imaging system of claim 15, wherein the set of sensors comprises sensors adapted to detect physiological characteristics of the user and the processor is adapted to determine affective information based at least in part on the physiological information.

20. The imaging system of claim 19, wherein the feedback comprises therapeutic feedback.

21. The imaging system of claim 20, wherein the imaging system is wearable.

22. The imaging system of claim 19, wherein the feedback comprises therapeutic feedback, intended to elicit a specific emotional response.

23. The imaging system of claim 15, wherein the set of sensors comprises a user camera adapted to capture images of a user's facial characteristics and sensors adapted to detect physiological characteristics of the user.

24. The imaging system of claim 15, wherein the imaging system further comprises a receiver adapted to receive feedback from the recipient and a presentation system to present the feedback to the user.

25. The imaging system of claim 15, wherein the set of sensors is further adapted to collect user identification data at capture and to transmit the user identification data with the collected affective information and the captured image.

26. The imaging system of claim 15, wherein the set of sensors is further adapted to provide a signal indicating the geographical location of the imaging system at capture.

27. An imaging system comprising:
  an image capture means for capturing an image of a scene being viewed by a user;
  affective sensor means separate from the image capture means for collecting affective information from the user at a time of the image capture; and
  a transmitting means for transmitting the scene image and affective information to a selected image receiver, said selected receiver being automatically identified by a determining means, said determining means making such identification based upon the collected affective information.

28. The imaging means of claim 27, wherein said affective sensor means detects facial characteristics of the user.

29. The imaging system of claim 27, wherein said affective sensor means detects physiological characteristics of the user.

30. The imaging system of claim 27, further comprising a receiving means for receiving feedback from the receiver and a presentation means for presenting the feedback to the user.

31. The imaging system of claim 27, further comprising a determining means for selecting the image receiver based upon analysis of the affective information.

32. The imaging system of claim 27, wherein the imaging system is incorporated in frame for glasses.

33. An image capture method comprising the steps of:
  capturing an image of a scene that a user is viewing at the time of capture and that does not include an image of the user;
  collecting affective information from the user at capture; and
  transmitting the scene image and affective information to an image receiver;
  wherein said collected affective information includes a combination of physiological characteristics, eye movement data and facial characteristics, and wherein said image receiver is identified based at least in part upon an emotional response determined from the collected affective information.

* * * * *